(12) United States Patent
Oshima

(10) Patent No.: US 8,808,752 B2
(45) Date of Patent: Aug. 19, 2014

(54) CONTROLLED RELEASE PARTICLES AND METHOD FOR PRODUCING THE SAME

(75) Inventor: Junji Oshima, Osaka (JP)

(73) Assignee: Japan Envirochemicals, Ltd., Osaka-shi, Osaka (JP)

( * ) Notice: Subject to any disclaimer, the term of this patent is extended or adjusted under 35 U.S.C. 154(b) by 0 days.

(21) Appl. No.: 13/394,960

(22) PCT Filed: Sep. 9, 2010

(86) PCT No.: PCT/JP2010/065521
§ 371 (c)(1),
(2), (4) Date: Mar. 8, 2012

(87) PCT Pub. No.: WO2011/030824
PCT Pub. Date: Mar. 17, 2011

(65) Prior Publication Data
US 2012/0172334 A1    Jul. 5, 2012

(30) Foreign Application Priority Data

Sep. 11, 2009    (JP) .................................. 2009-211143

(51) Int. Cl.
*A61K 9/50*    (2006.01)
*B01J 13/02*    (2006.01)
*B01J 13/18*    (2006.01)

(52) U.S. Cl.
USPC ............................................ 424/501; 254/4.7

(58) Field of Classification Search
CPC . A61K 9/1635; A61K 9/1694; A61K 9/1941; B01J 13/18; B41M 5/165
See application file for complete search history.

(56) References Cited

U.S. PATENT DOCUMENTS

| 4,656,205 A | 4/1987 | Walker et al. |
| 5,073,276 A | 12/1991 | Newlove et al. |

(Continued)

FOREIGN PATENT DOCUMENTS

| CA | 2082892 | 5/1993 |
| CA | 2321440 A1 | 8/1999 |

(Continued)

OTHER PUBLICATIONS

Notification Concerning Transmittal of International Preliminary Report on Patentability (Chapter I of the Patent Cooperation Treaty)(PCT/IB/326), International Preliminary Report on Patentability(PCT/IB/373), Notification of Transmittal of Translation of the International Preliminary Report on Patentability(Chapter I or Chapter II) (PCT/IB/338), Written Opinion of the International Search Authority in Japanese with English Translation (14 pages).

(Continued)

*Primary Examiner* — Carlos Azpuru
(74) *Attorney, Agent, or Firm* — Buchanan Ingersoll & Rooney P.C.

(57) ABSTRACT

Controlled release particles are obtained by dissolving a hydrophobic antibiotic compound in a hydrophobic polymerizable vinyl monomer without the presence of a solvent, thereby preparing a hydrophobic solution, the hydrophobic antibiotic compound having a melting point of 100° C. or less, a polar term $\delta_{p,compound}$ of 2 to 8 $[(J/cm^3)^{1/2}]$ of a solubility parameter ($\delta$) and a hydrogen bonding term $\delta_{h,compound}$ of 5.5 to 9.5 $[(J/cm^3)^{1/2}]$ of the solubility parameter ($\delta$), the solubility parameter ($\delta$) defined by Hansen and calculated by van Klevelen and Hoftyzer method; dispersing the hydrophobic solution in water; and polymerizing the polymerizable vinyl monomer in the presence of an oil-soluble initiator by radical polymerization, thereby producing a polymer having a polar term $\delta_{p,polymer}$ of 5 to 7 $[(J/cm^3)^{1/2}]$ and a hydrogen bonding term $\delta_{h,polymer}$ of 8 to 10 $[(J/cm^3)^{1/2}]$ of the solubility parameter ($\delta$).

3 Claims, 19 Drawing Sheets

SEM Photograph of Example 1 x3.0k    30 um

(56) References Cited

U.S. PATENT DOCUMENTS

| | | | |
|---|---|---|---|
| 6,365,066 | B1 | 4/2002 | Podszun et al. |
| 6,471,975 | B1 | 10/2002 | Banovetz et al. |
| 7,354,596 | B1 | 4/2008 | Banovetz et al. |
| 2007/0215000 | A1 | 9/2007 | Reybuck et al. |

FOREIGN PATENT DOCUMENTS

| | | |
|---|---|---|
| JP | 59-145265 | 8/1984 |
| JP | 60-132642 | 7/1985 |
| JP | 61-086941 | 5/1986 |
| JP | 5-212271 | 8/1993 |
| JP | 2008-218154 | 8/2000 |
| JP | 2001-247409 A | 9/2001 |
| JP | 2002-503679 A | 2/2002 |
| JP | 2002-513038 A | 5/2002 |
| JP | 2004-331625 A | 11/2004 |
| JP | 2008-239561 A | 10/2008 |
| JP | 2008-239562 A | 10/2008 |

OTHER PUBLICATIONS

International Search Report (PCT/ISA/210) issued on Nov. 22, 2010, by Japanese Patent Office as the International Searching Authority for International Application No. PCT/JP2010/065521.

Iconomopoulou, S.M., et al., "Incorporation of Low Molecular Weight Biocides Into Polystyrene-Divinyl Benzene Beads With Controlled Release Characteristics," Journal of Controlled Release, 2005, vol. 102, No. 1, pp. 223-233.

Vyas, S.P., et al.,"Formulation of Sustained Release Nitrofurantoin by Interfacial Copolymerization Method," Indian Drugs, 1980, vol. 18, No. 1 pp. 8-10.

Arun, A., et al., "In Vitro Drug Release Studies of 2-Hydroxyethyl Acrylate or 2-Hydroxypropyl Methacrylate-4-[1E,4E)-5-[4-Acryloyloxy)Phenyl]-3OXOPENTA-1,4-Dienyl} Phenyl Acrylate Copolymer Beads," Journal of Biomedical Materials Research Part B: Applied Biomaterials, 2005, vol. 73B, No. 2, pp. 291-300.

Croswell, Roger W. et al., "Suspension Polymerization for Preparation of Timed-Release Dosage Forms," Journal of Pharmaceutical Sciences, 1974, vol. 63, No. 3, pp. 440-442.

Masayoshi, Okubo, et al., "Production of Composite Polymer Particles Encapsulating Hinokitiol," Japan Chemical Society Lecture Preliminary Drafts, 2001, vol. 79, No. 1, p. 425.

Kassem, Aly A., "Formulation and Evaluation of Controlled Dissolution Phenobarbitone Macremolecular Products Employing In-Situ Suspension Polymerization With Methylmethacrylate," Egyptian Journal of Pharmaceutical Sciences, 1978, vol. 19, No. 1-4, pp. 143-162.

Notice of Reasons for Refusal issued on Feb. 21, 2014, by the Japanese Patent Office in Japanese Patent Application No. 2010-201604, and an partial English translation of the Notice. (7 pages).

Kosmetik, et al. "Perlpolymerisate, Eine Neue Perorale Darreichungsform und Ihre Beeinflussung Durch Arzneistoffe," Praparative Pharmazie, 1970, vol. 6, No. 9/10, pp. 149-154.

FIG.1 SEM Photograph of Example 1
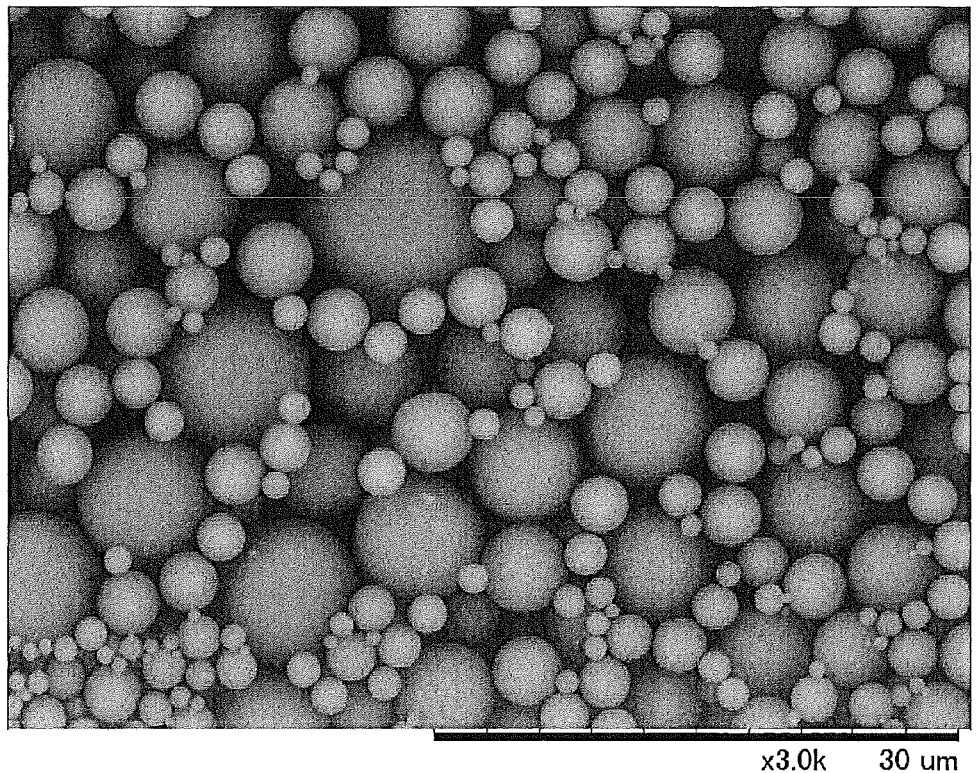
FIG.2 SEM Photograph of Example 5
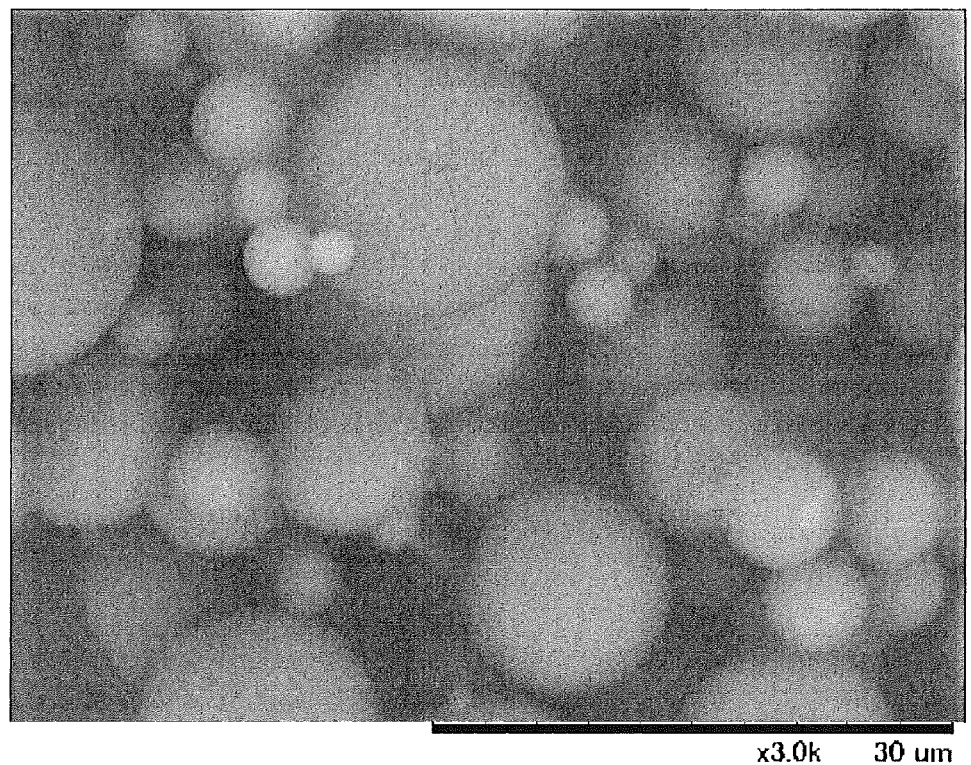

SEM Photograph of Example 8 x3.0k  30 um

SEM Photograph of Example 14 x1.0k  100 um

SEM Photograph of Example 15 x1.0k  100 um

SEM Photograph of Example 16 x1.0k  100 um

SEM Photograph of Comparative Example 2 x1.0k  100 um

SEM Photograph of Comparative Example 4 x1.0k  100 um

SEM Photograph of Comparative Example 5 x1.0k  100 um

SEM Photograph of Comparative Example 6 x1.0k  100 um

FIG.11 TEM Photograph of Example 1

TEM Photograph of Example 9

10 microns

FIG.13 TEM Photograph of Example 10

10 microns

TEM Photograph of Example 11

2 microns

FIG.15 TEM Photograph of Example 12

10 microns

TEM Photograph of Example 13

10 microns

CONTROLLED RELEASE PARTICLES AND METHOD FOR PRODUCING THE SAME

TECHNICAL FIELD

The present invention relates to controlled release particles and a method for producing the same, in particular, to controlled release particles that allow controlled-release of an antibiotic compound and to a method for producing the same.

BACKGROUND ART

It is known that micro-encapsulation of antibiotic compounds such as a sterilizer, an antiseptic, and a fungicide allow controlled-release of the antibiotic compound to ensure lasting effects.

For example, a method for producing a microbial growth inhibitor-containing microcapsule (for example, see Patent Document 1 below) has been proposed: in the method, an oil phase including a microbial growth inhibitor and a polyisocyanate component, and an aqueous phase including an active hydrogen group-containing component are blended and dispersed, thereby allowing interfacial polymerization.

CITATION LIST

Patent Document

Patent Document 1: Japanese Unexamined Patent Publication No. 2001-247409

SUMMARY OF THE INVENTION

Problem to be Solved by the Invention

However, in the interfacial polymerization described in Patent Document 1 above, the polyisocyanate component and the active hydrogen group-containing component, that is, two types of film-forming components, are blended in the oil phase and in the aqueous phase, respectively, to prepare two phases. This increases the number of processes to that extent, and therefore may lead to complication of the production process, an increase in ingredient costs, and an increase in production costs.

An object of the present invention is to provide controlled release particles excellent in controlled release properties easily at low-cost; and a method for producing the same.

Means for Solving the Problem

The present inventor made an energetic study on the controlled release particles and the production method thereof of the above object, and found out that controlled release particles that are excellent in controlled release properties can be obtained easily at low cost as follows, and as a result of further advancing the study, accomplished the present invention: by producing a polymer having a polar term $\delta_{p,polymer}$ and a hydrogen bonding term $\delta_{h,polymer}$ of the solubility parameter ($\delta$) in a predetermined range as follows: a hydrophobic antibiotic compound having a melting point of 100° C. or less and having a polar term $\delta_{p,compound}$ and a hydrogen bonding term $\delta_{h,compound}$ of the solubility parameter ($\delta$) in a predetermined range is dissolved in a hydrophobic polymerizable vinyl monomer without the presence of a solvent, thereby preparing a hydrophobic solution; and the hydrophobic solution is dispersed in water, thereby allowing the polymerizable vinyl monomer to undergo radical polymerization.

That is, the present invention provides, (1) controlled release particles obtained by dissolving a hydrophobic antibiotic compound in a hydrophobic polymerizable vinyl monomer without the presence of a solvent, thereby preparing a hydrophobic solution, the hydrophobic antibiotic compound having a melting point of 100° C. or less, a polar term $\delta_{p,compound}$ of 2 to 8 [(J/cm³)$^{1/2}$] of a solubility parameter ($\delta$), and a hydrogen bonding term $\delta_{h,compound}$ of 5.5 to 9.5 [(J/cm³)$^{1/2}$] of the solubility parameter ($\delta$), the solubility parameter ($\delta$) being defined by Hansen and calculated by van Krevelen and Hoftyzer method; dispersing the hydrophobic solution in water; and polymerizing the polymerizable vinyl monomer in the presence of an oil-soluble initiator by radical polymerization, thereby producing a polymer having a polar term $\delta_{p,polymer}$ of 5 to 7 [(J/cm³)$^{1/2}$] and a hydrogen bonding term $\delta_{h,polymer}$ of 8 to 10 [(J/cm³)$^{1/2}$] of the solubility parameter ($\delta$), (2) the controlled release particles of (1), wherein the value of $\Delta\delta_p$ obtained by deducting the polar term $\delta_{p,compound}$ of the antibiotic compound from the polar term $\delta_{p,polymer}$ of the polymer is −1.1 to 2.7 [(J/cm³)$^{1/2}$], and the value of $\Delta\delta_h$ obtained by deducting the hydrogen bonding term $\delta_{h,compound}$ of the antibiotic compound from the hydrogen bonding term $\delta_{h,polymer}$ of the polymer is 0 to 4.2 [(J/cm³)$^{1/2}$], (3) the controlled release particles of (1), wherein the mixing ratio of the antibiotic compound relative to the polymerizable vinyl monomer is 0.11 to 1.5 on a weight basis, (4) A method for producing controlled release particles, the method comprising the steps of dissolving a hydrophobic antibiotic compound in a hydrophobic polymerizable vinyl monomer without the presence of a solvent, thereby preparing a hydrophobic solution, the hydrophobic antibiotic compound having a melting point of 100° C. or less, and a polar term $\delta_{p,compound}$ of 2 to 8 [(J/cm³)$^{1/2}$] of a solubility parameter ($\delta$), and a hydrogen bonding term $\delta_{h,compound}$ of 5.5 to 9.5 [(J/cm³)$^{1/2}$] of the solubility parameter ($\delta$), the solubility parameter ($\delta$) being defined by Hansen and calculated by van Krevelen and Hoftyzer method;

dispersing the hydrophobic solution in water, and polymerizing the polymerizable vinyl monomer in the hydrophobic solution dispersed in water in the presence of an oil-soluble initiator by radical polymerization, thereby producing a polymer having a polar term $\delta_{p,polymer}$ of 5 to 7 [(J/cm³)$^{1/2}$] and a hydrogen bonding term $\delta_{h,polymer}$ of 8 to 10 [(J/cm³)$^{1/2}$] of the solubility parameter ($\delta$), (5) The method for producing controlled release particles of (4), wherein the value of $\Delta\delta_p$ obtained by deducting the polar term $\delta_{p,compound}$ of the antibiotic compound from the polar term $\delta_{p,polymer}$ of the polymer is −1.1 to 2.7 [(J/cm³)$^{1/2}$], and the value of $\Delta\delta_h$ obtained by deducting hydrogen bonding term $\delta_{h,compound}$ of the antibiotic compound from the hydrogen bonding term $\delta_{h,polymer}$ of the polymer is 0 to 4.2 [(J/cm³)$^{1/2}$].

Effect of the Invention

With the method for producing polymer microparticles of the present invention, a polymer having a polar term $\delta_{p,polymer}$ and a hydrogen bonding term $\delta_{h,polymer}$ of the solubility parameter ($\delta$) in predetermined ranges is produced by polymerizing a hydrophobic polymerizable monomer in which an antibiotic compound having a polar term $\delta_{p,compound}$ and a hydrogen bonding term $\delta_{h,compound}$ of the solubility parameter ($\delta$) in predetermined ranges is dissolved. This allows easy preparation of ingredients, simple production steps, and furthermore, decreased ingredient costs; therefore, production costs can be decreased.

Thus, controlled release particles having excellent controlled release properties and exhibiting excellent lasting effects can be obtained easily at low cost.

Furthermore, because the hydrophobic solution is prepared without using a solvent, environmental burden can be reduced.

BRIEF DESCRIPTION OF THE DRAWINGS

FIG. 1 shows an image-processed SEM photograph of controlled release particles of Example 1.

FIG. 24 shows a graph of controlled release properties test of Comparative Examples 1 and 2.

EMBODIMENT OF THE INVENTION

Figure 3:
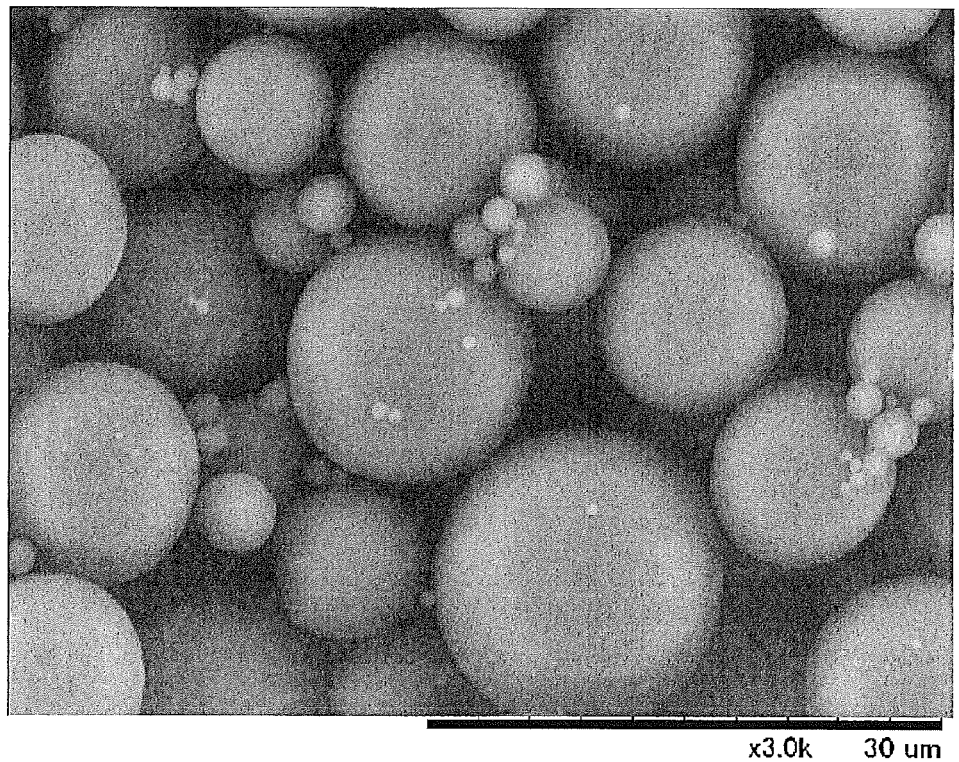
FIG. 3 shows an image-processed SEM photograph of controlled release particles of Example 8.
Figure 4:
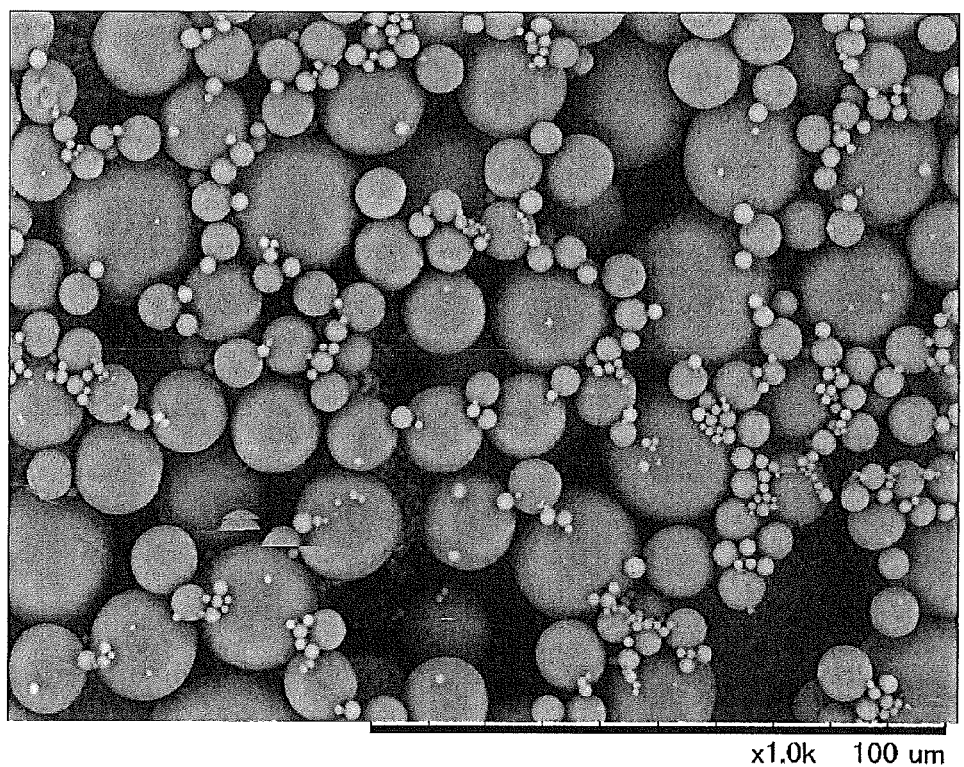
FIG. 4 shows an image-processed SEM photograph of controlled release particles of Example 14.
Figure 5:
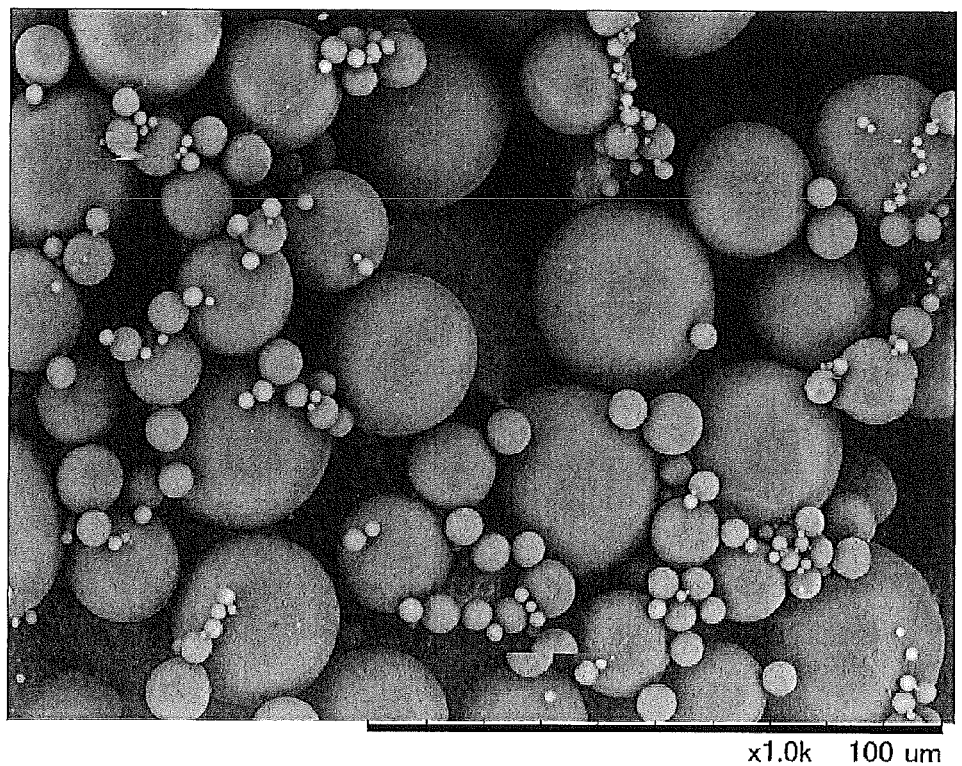
FIG. 5 shows an image-processed SEM photograph of controlled release particles of Example 15.
Figure 6:
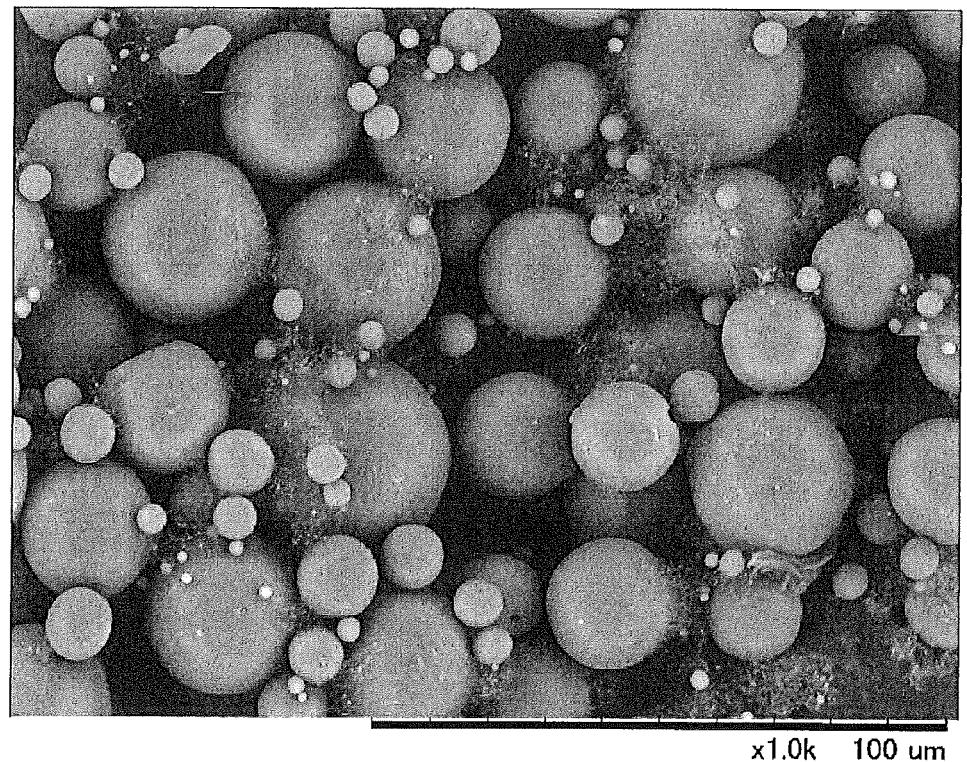
FIG. 6 shows an image-processed SEM photograph of controlled release particles of Example 16.

Controlled release particles of the present invention are obtained by producing a polymer as follows: a hydrophobic antibiotic compound is dissolved in a hydrophobic polymerizable vinyl monomer, thereby preparing a hydrophobic solution; and the hydrophobic solution is dispersed in water, thereby allowing the polymerizable vinyl monomer to undergo radical polymerization.

The antibiotic compound has, for example, at least two functional moieties that are capable of interacting with the polymer of the polymerizable vinyl monomer.

Examples of such functional moieties include polar functional groups such as a carbonyl group, a nitro group, an amino group, a cyano group, a phosphate group, and a carboxyl group; polar bonds containing a polar group such as a carboxylate bond, a phosphate bond, a urea bond, and a carbon-halogen bond; and conjugated cyclic portions such as a benzene ring, and further a conjugated heterocyclic ring such as a triazine ring, an imidazole ring, and an isothiazoline ring.

The antibiotic compound has a molecular weight of, for example, 200 to 600, preferably 200 to 500.

When the antibiotic compound has a molecular weight exceeding the above-described range, miscibility of the antibiotic compound with the polymer may be reduced. On the other hand, when the antibiotic compound has a molecular weight below the above-described range, there is a case where the antibiotic compound remains in the aqueous phase during suspension polymerization (described later), and after the suspension polymerization, the antibiotic compound separates out, solidifying the suspension liquid.

The antibiotic compound has a melting point of 100° C. or less, preferably 90° C. or less, and more preferably 80° C. or less. When the antibiotic compound has a melting point exceeding the above-described range, there may be a case where the antibiotic compound is not easily encapsulated in the controlled release particles and separates outside the controlled release particles, and even if the antibiotic compound is encapsulated in the controlled release particles, controlled-release of the antibiotic compound to the outside the controlled release particles may not be allowed.

To be specific, the antibiotic compound is selected from a sterilizer, an antibacterial agent, an antiseptic, an antialgae, a fungicide, a herbicide, an insecticide, an attractant, a repellent, a rodenticide, etc. having antibiotic activity such as, for example, sterilizing, antibacterial, antiseptic, antialgae, antifungal, and insecticidal activity. Examples of these compounds having antibiotic activity include sterilizing antiseptic antialgae fungicides such as an iodine compound, a triazole compound, a carbamoyl imidazole compound, a dithiol compound, an isothiazoline compound, a nitro alcohol compound, and p-hydroxybenzoate ester; and termite control agent (termite killers) such as a pyrethroid compound, a neonicotinoid compound, an organic chlorine compound, an organic phosphorus compound, a carbamate compound, and an oxadiazon compound.

Examples of iodine compounds include 3-iodo-2-propynylbutylcarbamate (IPBC), 1-[[(3-iodo-2-propynyl)oxy]methoxy]-4-methoxybenzene, and 3-bromo-2,3-diiodo-2-propenyl ethyl carbonate.

Examples of triazole compounds include 1-[2-(2,4-dichlorophenyl)-4-n-propyl-1,3-dioxolane-2-ylmethyl]-1H-1,2,4-triazole (propiconazole), and bis(4-fluorophenyl)methyl (1H-1,2,4-triazole-1-ylmethylsliane (also called: flusilazole, 1-[[bis(4-fluorophenyl)methylsilyl]methyl]-1H-1-1,2,4-triazole).

Examples of carbamoyl imidazole compounds include N-propyl-N-[2-(2,4,6-trichloro-phenoxy)ethyl]imidazole-1-carboxamide (prochloraz).

Examples of dithiol compounds include 4,5-dichloro-1,2-dithiol-3-one.

Examples of isothiazoline compounds include 2-n-octyl-4-isothiazoline-3-one (OIT) and 5-chloro-2-methyl-4-isothiazoline-3-one (Cl-MIT).

Examples of nitro alcohol compounds include 2,2-dibromo-2-nitro-1-ethanol (DBNE).

Examples of p-hydroxybenzoate esters include butyl p-hydroxybenzoate and propyl p-hydroxybenzoate.

Examples of pyrethroid compounds include pyrethrin obtained from pyrethrum, cinerin, and jasmoline; and also include allethrin, bifenthrin, acrinathrin, α-cypermethrin, tralomethrin, cyfluthrin ((RS)-α-cyano-4-fluoro-3-phenoxybenzyl-(1RS,3RS)-(1RS,3RS)-3-(2,2-dichlorovinyl)-2,2-methylcyclopropane carboxylate, to be specific, a mixture of isomer I ((1R-3R-αR)+(1S-3S-αS))[melting point: 57° C.], isomer II ((1R-3R-S)+(1S-3S-αR))[melting point: 74° C.], and isomer III ((1R-3S-αR)+(1S-3R-αS)))[melting point: 66° C.]), cyphenothrin, prallethrin, ethofenprox, silafluofen, and fenvalerate derived therefrom.

Examples of neonicotinoid compounds include (E)-$N^1$-[(6-chloro-3-pyridyl)methyl]-$N^2$-cyano-$N^1$-methylacetamidine (acetamiprid).

Examples of organic chlorine compounds include Kelthane.

Examples of organic phosphorus compounds include phoxim, pyridaphenthion, fenitrothion, tetrachlorvinphos, diehlofenthion, and propetamphos.

Examples of carbamate compounds include fenobucarb and propoxur.

Examples of oxadiazon compounds include indoxacarb.

Examples of herbicides include pyraclonil, pendimethalin, and indanofan.

Examples of insecticides include pyriproxyfen.

Examples of repellents include Deet.

The antibiotic compound is substantially hydrophobic, and, for example, has a quite low water solubility at room temperature (20 to 30° C., to be more specific, 25° C.), to be specific, for example, a solubility at room temperature of, on a weight basis, 1 part by weight/100 parts by weight of water (10000 ppm) or less, preferably 0.5 parts by weight/100 parts by weight of water (5000 ppm) or less, and more preferably 0.1 parts by weight/100 parts by weight of water (1000 ppm) or less; and on a volume basis, for example, 1 g/100 mL of water or less, preferably 0.5 g/100 mL of water or less, and more preferably 0.1 g/100 mL of water or less.

When the antibiotic compound has a water solubility exceeding the above-described range, when polymerizing the polymerizable vinyl monomer (suspension polymerization), the antibiotic compound easily leaks out to the outside (that is, aqueous phase) of the controlled release particles, and after the polymerization, the antibiotic compound dissolved in the aqueous phase separates out, and therefore synthesis of controlled release particles sufficiently encapsulating the antibiotic compound becomes difficult.

These antibiotic compounds can be used alone or in combination of two or more.

The above-described antibiotic compound may contain, for example, in the production processes, impurities having a melting point of outside the above-described range at an appropriate proportion. To be specific, a mixture of isomer I (melting point: 57° C.), isomer II (melting point: 74° C.), and isomer III (melting point: 66° C.) of cyfluthrin contains, for example, an impurity of isomer IV (melting point 102° C.).

The polymerizable vinyl monomer is, for example, a monomer having at least one vinyl group in its molecule.

To be specific, examples of polymerizable vinyl monomers include a (meth)acrylate monomer, a (meth)acrylic acid monomer, an aromatic vinyl monomer, a vinyl ester monomer, a maleate monomer, vinyl halide, vinylidene halide, and a nitrogen-containing vinyl monomer.

Examples of (meth)acrylate monomers include methacrylates and acrylates, to be specific, methyl(meth)acrylate, ethyl (meth)acrylate, n-propyl(meth)acrylate, iso-propyl(meth) acrylate, n-butyl(meth)acrylate, iso-butyl(meth)acrylate, tert-butyl(meth)acrylate, cyclohexyl(meth)acrylate, and 2-methoxyethyl(meth)acrylate.

Examples of (meth)acrylic acid monomer include methacrylic acid and acrylic acid.

Examples of aromatic vinyl monomers include styrene, p-methyl styrene, α-methyl styrene, and vinyltoluene.

Examples of vinyl ester monomers include vinyl acetate and vinyl propionate.

Examples of maleate monomers include dimethyl maleate, diethyl maleate, and dibutyl maleate.

Examples of vinyl halides include vinyl chloride and vinyl fluoride.

Examples of vinylidene halides include vinylidene chloride and vinylidene fluoride.

Examples of nitrogen-containing vinyl monomers include (meth)acrylonitrile, N-phenylmaleimide, and vinylpyridine.

The polymerizable vinyl monomer is substantially hydrophobic, and for example, has a significantly low water solubility at room temperature, to be specific, a solubility at room temperature of, for example, 10 parts by weight/100 parts by weight of water or less, preferably 8 parts by weight/100 parts by weight of water or less.

Of the above-described monomers, for example, an antibiotic compound-miscible monomer (hereinafter sometimes simply referred to as a miscible monomer) that is highly miscible with the above-described antibiotic compound and is capable of dissolving the antibiotic compound is selected.

These miscible monomers can be used alone or in combination of two or more.

As the miscible monomer, preferably the same kind of (meth)acrylate monomer is used singly, different types of (meth)acrylate monomers are used in combination, or (meth) acrylate monomer and (meth)acrylic acid monomer are used in combination.

More preferably, methyl methacrylate (MMA) is used singly; methyl methacrylate and C2 to 4 alkyl(meth)acrylate are used in combination, or a methyl methacrylate and a methacrylic acid are used in combination.

Examples of C2 to 4 alkyl(meth)acrylate used in combination with methyl methacrylate include ethyl(meth)acrylate, n-propyl(meth)acrylate, iso-propyl(meth)acrylate, n-butyl (meth)acrylate, iso-butyl(meth)acrylate, and tent-butyl (meth)acrylate.

When different types of (meth)acrylate monomers are used in combination, the mixing ratio of methyl methacrylate relative to 100 parts by weight of the miscible monomer (including the crosslinkable monomer to be described later) is, for example, 20 parts by weight or more, preferably 40 parts by weight or more, and for example, 99 parts by weight or less.

When a (meth)acrylate monomer and a (meth)acrylic acid monomer are used in combination, the mixing ratio of the (meth)acrylic acid monomer relative to 100 parts by weight of the miscible monomer including the crosslinkable monomer is, for example, below 30 parts by weight, 20 parts by weight or less, and 1 part by weight or more, preferably 3 parts by weight or more.

A combination of the antibiotic compound and the miscible monomer is selected so that the polymer of the polymerizable vinyl monomer and the antibiotic compound are miscible at a polymerization temperature (heating temperature) to be described later.

The polymerizable vinyl monomer can contain a crosslinkable monomer as the miscible monomer.

The crosslinkable monomer is blended as necessary to adjust controlled release properties of the controlled release particles, and examples of the crosslinkable monomer include mono or polyethylene glycol di(meth)acrylate such as ethylene glycol di(meth)acrylate and diethylene glycol di(meth)acrylate; alkane diol di(meth)acrylate such as 1,3-propanediol di(meth)acrylate, 1,4-butanediol di(meth)acrylate, and 1,5-pentanediol di(meth)acrylate; alkane polyol poly(meth)acrylate such as trimethylolpropane tri(meth)acrylate and pentaerythritol tetra(meth)acrylate; allyl monomers such as allyl(meth)methacrylate, and triallyl(iso)cyanurate; and divinyl monomers such as divinylbenzene.

As the crosslinkable monomer, a monomer having a molecule structure that is similar to that of the miscible monomer excluding the crosslinkable monomer is selected to ensure miscibility with the miscible monomer excluding the crosslinkable monomer; to be specific, when the miscible monomer excluding the crosslinkable monomer contains methyl methacrylate, preferably, ethylene glycol dimethacrylate (EGDMA) or trimethylolpropane trimethacrylate (TMPTMA) is selected as the crosslinkable monomer.

The mixing ratio of the crosslinkable monomer relative to 100 parts by weight of the polymerizable vinyl monomer (miscible monomer) is, for example, 1 to 100 parts by weight, preferably 10 to 80 parts by weight.

In the present invention, as the antibiotic compound and the polymerizable vinyl monomer, a combination of an antibiotic compound having a polar term $\delta_{p,compound}$ of 2 to 8 $[(J/cm^3)^{1/2}]$ and a hydrogen bonding term $\delta_{h,compound}$ of 5.5 to 9.5 $[(J/cm^3)^{1/2}]$ of the solubility parameter ($\delta$) defined by Hansen and calculated by van Krevelen and Hoftyzer method; and a polymerizable vinyl monomer that produces a polymer having a polar term $\delta_{p,polymer}$ of 5 to 7 $[(J/cm^3)^{1/2}]$ and a hydrogen bonding term $\delta_{h,polymer}$ of 8 to 10 $[(J/cm^3)^{1/2}]$ of the solubility parameter ($\delta$) are selected.

The indexes "compound" and "polymer" in each term $\delta$ ($\delta_p$ and $\delta_h$) represent the antibiotic compound and the polymer, respectively.

The polar term $\delta_p$ and the hydrogen bonding term $\delta_h$ of the solubility parameter ($\delta$) defined by Hansen and calculated by van Krevelen and Hoftyzer method depend on the types and the number of the atomic group (including chemical bond or substituent), to be specific, represented by following formulas (1) and (2), respectively.

[Mathematical Formula 1]

$$\delta_p = \frac{\sqrt{\sum F_{pi}^2}}{V} \quad (1)$$

(where $F_p$ represents polar component of the molar attraction function, and V represents molar volume)

[Mathematical Formula 2]

$$\delta_h = \sqrt{\frac{\sum E_{hi}}{V}} \quad (2)$$

(where $E_h$ represents contribution of the hydrogen bonding forces to the cohesive energy, and V represents molar volume.)

Values of the above-described $F_p$, $E_h$, and V are described in "Properties of Polymers" (3rd Edition, Chapter 7, pp 189 to 225, written by van Krevelen, ELSEVIER, issued in 2003) by atomic group.

$F_p$ and $E_h$ of substituent —I, >Si<, =N— and =C— are not described in the above-described document, but calculated by professor Hideki Yamamoto of Kansai University by the following method.

First, an example of the calculation method for $F_p$ of substituent —I is given.

Ten compounds containing substituent —I described in "Hansen Solubility Parameters, A User's Handbook" (written by Charles Hansen, pp 347 to 483 (Appendix), CRC Press, issued in 2007) are randomly selected, and the left side of the above-described formula (1) is substituted by the value of compound $\delta_p$ described in the above-described document. Furthermore, the right side of the above-described formula (2) is substituted by values of V of all atomic groups of the ten compounds selected as described above, and $F_p$ of the atomic group excluding the substituent —I, while $F_p$ of the substituent —I in the right side is rendered unknown.

Then, the equation in which $\delta_p$ of the compound and V of all atomic groups are known, and $F_p$ of the atomic group excluding the substituent is known, and $F_p$ of substituent —I is unknown is solved, and the average of the solution ($F_p$) of the ten compound as $F_p$ of substituent —I is calculated.

$F_p$ of the substituent >Si<, =N—, and =C— is also calculated in the above-described manner.

$E_h$ of the substituent —I, >Si<, =N—, and =C— can also be calculated in the above-described manner.

The above-described calculation process is recorded in a computer as a program, and optimized.

$F_p$ and $E_h$ of the substituent —I, >Si<, =N—, and =C— calculated as described above are noted below.

—I $F_p$:0 $(J^{1/2} \cdot cm^{3/2} \cdot mol^{-1})$ $E_h$:0$(J \cdot mol^{-1})$ >Si< $F_p$:0 $(J^{1/2} \cdot cm^{3/2} \cdot mol^{-1})$ $E_h$:0$(J \cdot mol^{-1})$ =N— $F_p$:800 $(J^{1/2} \cdot cm^{3/2} \cdot mol^{-1})$ $E_h$:3000$(J \cdot mol^{-1})$ =C— $F_p$:0 $(J^{1/2} \cdot cm^{3/2} \cdot mol^{-1})$ $E_h$:0$(J \cdot mol^{-1})$ Next, as an example of polymers, polymethyl methacrylate (PMMA), i.e., a polymer of methyl methacrylate, is given as an example, and a polar term $\delta_{p,PMMA}$ and a hydrogen bonding term $\delta_{h,PMMA}$ of the solubility parameter ($\delta$) of polymethyl methacrylate is calculated.

1. Polar Term $\delta_p$ and Hydrogen Bonding Term $\delta_h$ of Homopolymer (1) Structural Formula of Polymethyl Methacrylate Polymethyl methacrylate is represented by formula (3) below.

[Chemical Formula 1]

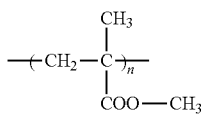

(3)

(where n represents degree of polymerization)
(2) Polar Term $\delta_{p,PMMA}$
$F_p$ and V of atomic groups in the monomer unit ($-CH_2-C(CH_3)COOCH_3-$) of the above-described formula (3) are shown below.

$-CH_3$ $F_p$:0 $(J^{1/2} \cdot cm^{3/2} \cdot mol^{-1})$

V:33.5 $(cm^3 \cdot mol)$ $-CH_2-$ $F_p$:0 $(J^{1/2} \cdot cm^{3/2} \cdot mol^{-1})$ V:16.1 $(cm^3 \cdot mol)$ $>C<$ $F_p$:0 $(J^{1/2} \cdot cm^{3/2} \cdot mol^{-1})$ V:-19.2 $(cm^3 \cdot mol)$ $-COO-$ $F_p$: 490 $(J^{1/2} \cdot cm^{3/2} \cdot mol^{-1})$ V:18 $(cm^3 \cdot mol)$ Therefore, polar term $\delta_{p,monomer\ unit}$ of the monomer unit is calculated, as shown in formula (4) below, to be 5.98 $[(J/cm^3)^{1/2}]$.

[Mathematical Formula 3]

$$\delta_p = \frac{\sqrt{\sum F_{pi}^2}}{V}$$

$$= \frac{\sqrt{0^2 + 0^2 + 0^2 + 490^2}}{2 \times 33.52 + 16.1 + (-19.2) + 18}$$

$$= 5.98[(J/cm^3)^{1/2}]$$

(4)

Then, the polar term $\delta_{p,monomer\ unit}$ of the above-described monomer unit is rendered the polar term $\delta_{p,PMMA}$ of polymethyl methacrylate, having a repeating structure of the monomer unit.
(3) Hydrogen Bonding Term $\delta_{h,PMMA}$
$E_h$, of the atomic groups in the monomer unit ($-CH_2-C(CH_3)COOCH_3-$) of the above-described formula (3) is shown below.

$-CH_3$ $E_h$:0$(J \cdot mol^{-1})$ $-CH_2-$ $E_h$:0$(J \cdot mol^{-1})$ $>C<$ $E_h$:0$(J \cdot mol^{-1})$ $-COO-$ $E_h$:7000 $(J \cdot mol^{-1})$ Therefore, the hydrogen bonding term $\delta_{h,monomer\ unit}$ of the monomer unit is calculated, as shown in formula (5) below, to be 9.25 $[(J/cm^3)^{1/2}]$.

[Mathematical Formula 4]

$$\delta_h = \sqrt{\frac{\sum E_{hi}}{V}}$$

$$s = \sqrt{\frac{0 + 0 + 0 + 7000}{2 \times 33.5 + 16.1 + (-19.2) + 18}}$$

$$= 9.25[(J/cm^3)^{1/2}]$$

(5)

Then, the above-described hydrogen bonding term $\delta_{h,polymer}$ of the monomer unit is rendered the hydrogen bonding term $\delta_{h,PMMA}$ of polymethyl methacrylate, having a repeating structure of the monomer unit.
2. Polar Term $\delta_p$ and Hydrogen Bonding Term $\delta_h$ of Copolymer
Next, polar term $\delta_p$ and hydrogen bonding term $\delta_h$ of a copolymer is calculated.
By multiplying the polar term $\delta_{p,monomer\ unit}$ of monomer units by the weight ratio of the monomer, and by adding these, the polar term $\delta_{p,copolymer}$ of the solubility parameter ($\delta$) of the copolymer is calculated. Also, by multiplying the hydrogen bonding term $\delta_{h,monomer\ unit}$ of the monomer units by the weight ratio of the monomer, and adding these, the hydrogen bonding term $\delta_{h,copolymer}$ of the solubility parameter ($\delta$) of the copolymer is calculated.
As an example of the copolymer, a polymethyl methacrylate-ethylene glycol dimethacrylate copolymer (PMMA-EGDMA), i.e., a copolymer of a monomer containing methyl methacrylate and ethylene glycol dimethacrylate in a weight ratio of 90:10, is used, and its polar term $\delta_{p,PMMA-EGDMA}$ and the hydrogen bonding term $\delta_{h,PMMA-EGDMA}$ of the solubility parameter ($\delta$) are calculated.
(1) Polar Term $\delta_{p,PMMA-EGDMA}$
The polar term $\delta_{p,MMA\ unit}$ of the monomer unit of methyl methacrylate is, as calculated above, 5.98 $[(J/cm^3)^{1/2}]$.
The polar term $\delta_{p,EGDMA}$ of the monomer unit of ethylene glycol dimethacrylate is calculated in the same manner as above, and determined to be 5.37 $[(J/cm^3)^{1/2}]$.
The polar term $\delta_{p,PMMA-EGDMA}$ of the copolymer is calculated as shown in formula (6) below.

$$\delta_{p,PMMA-EGDMA} = (90/100)\delta_{p,MMA\ unit} + (10/100)\delta_{p,EGDMA\ unit} \quad (6)$$

$$= (90/100) \times 5.98 + (10/100) \times 5.37$$

$$= 5.92[(J/cm^3)^{1/2}]$$

(2) Hydrogen Bonding Term $\delta_{h,PMMA-EGDMA}$
The hydrogen bonding term $\delta_{h,MMA\ unit}$ of the monomer unit of methyl methacrylate is 9.25 $[(J/cm^3)^{1/2}]$.
The hydrogen bonding term $\delta_{h,EGDMA}$ of the monomer unit of ethylene glycol dimethacrylate is 10.42 $[(J/cm^3)^{1/2}]$.
The hydrogen bonding term $\delta_{h,PMMA-EGDMA}$ of the copolymer is calculated as shown in formula (7) below.

$$\delta_{h,PMMA-EDGMA} = (90/100)\delta_{h,MMA\ unit} + (10/100)\delta_{h,EGDMA\ unit} \quad (7)$$

$$= (90/100) \times 9.25 + (10/100) \times 10.42$$

$$= 9.36[(J/cm^3)^{1/2}]$$

The polar term $\delta_{p,polymer}$ of the solubility parameter ($\delta$) of the polymer is preferably 5 to 6.5 $[(J/cm^3)^{1/2}]$, the hydrogen bonding term $\delta_{h,polymer}$ of the solubility parameter ($\delta$) of the polymer is preferably 9 to 10 [(J/cm$^3$)$^{1/2}$].

When the polar term $\delta_{p,polymer}$ and/or the hydrogen bonding term $\delta_{h,polymer}$ of the polymer is below the above-described range, there may be a case where hydrophobicity of the polymer becomes excessively high and sufficient miscibility with the antibiotic compound is not obtained, and even if miscibility is obtained, the antibiotic compound leaks to the outside of the controlled release particles during polymerization (suspension polymerization), making synthesis of controlled release particles in which the antibiotic compound is sufficiently encapsulated difficult.

On the other hand, when the polar term $\delta_{p,polymer}$ and/or the hydrogen bonding term $\delta_{h,polymer}$ of the polymer exceeds the above-described range, there may be a case where hydrophilicity of the polymer becomes excessively high and sufficient miscibility with the antibiotic compound cannot be obtained, and even if miscibility could be obtained, interfacial free energy with the aqueous phase in the suspension polymerization is lowered, and antibiotic compound leaks to the outside of the controlled release particles during the suspension polymerization, making synthesis of controlled release particles in which the antibiotic compound is sufficiently encapsulated difficult.

3. Polar term $\delta_{p,compound}$ and Hydrogen Bonding Term $\delta_{h,compound}$ of Solubility ($\delta$) of Antibiotic Compound The polar term $\delta_{p,compound}$ and the hydrogen bonding term $\delta_{h,compound}$ of the solubility ($\delta$) of the antibiotic compound is also calculated in the same manner as that of the above-described monomer unit.

Table 1 shows the results of the calculated polar term $\delta_{p,compound}$ and hydrogen bonding term $\delta_{h,compound}$ of antibiotic compounds, i.e., IPBC, OIT, cyfluthrin, propiconazole, prochloraz, and flusilazole.

TABLE 1

| Antibiotic Compound | Polar Term $\delta_{p,\,compound}$ [(J/cm$^3$)$^{1/2}$] | Hydrogen Bonding Term $\delta_{h,\,compound}$ [(J/cm$^3$)$^{1/2}$] |
| --- | --- | --- |
| IPBC | 3.23 | 7.83 |
| OIT | 5.47 | 5.87 |
| Cyfluthrin | 3.46 | 6.09 |
| Propiconazole | 6.55 | 9.44 |
| Prochloraz | 7.07 | 8.31 |
| Flusilazole | 5.95 | 6.85 |

The polar term $\delta_{p,compound}$ of solubility parameter ($\delta$) of the antibiotic compound is preferably 3 to 7 [(J/cm$^3$)$^{1/2}$] and the hydrogen bonding term $\delta_{h,compound}$ is preferably 5.8 to 9.5 [(J/cm$^3$)$^{1/2}$].

When the polar term $\delta_{p,compound}$ and/or the hydrogen bonding term $\delta_{h,compound}$ of the antibiotic compound is below the above-described range, there may be a case where hydrophobicity of the antibiotic compound becomes excessively high and sufficient miscibility with the polymer cannot be obtained.

On the other hand, when the polar term $\delta_{p,compound}$ and/or the hydrogen bonding term $\delta_{h,compound}$ of the antibiotic compound exceed the above-described range, there may be a case where hydrophilicity of the antibiotic compound becomes excessively high and the antibiotic compound easily leaks to the outside of the controlled release particles, making synthesis of the controlled release particles in which the antibiotic compound is sufficiently encapsulated difficult.

4. Difference in Polar Term $\delta_p$ ($\Delta\delta_p$) and Difference in Hydrogen Bonding Term $\delta_h$ ($\Delta\delta_h$) of Solubility Parameter In the present invention, the value of $\Delta\delta_p$ (=$\delta_{p,polymer}$ − $\delta_{p,compound}$) deducting the polar term $\delta_{p,compound}$ of the antibiotic compound from the polar term $\delta_{p,polymer}$ of the polymer of the solubility parameter ($\delta$) is, for example, −1.1 to 2.7 [(J/cm$^3$)$^{1/2}$].

The value of $\Delta\delta_h$ (=$\delta_{h,polymer}$ − $\delta_{h,compound}$) deducting the hydrogen bonding term $\delta_{h,compound}$ of the antibiotic compound from the hydrogen bonding term $\delta_{h,polymer}$ of the polymer is, for example, 0 to 4.2 [(J/cm$^3$)$^{1/2}$].

When $\Delta\delta_p$ and $\Delta\delta_h$ are within the above-described range, excellent miscibility of the antibiotic compound and the polymer can be ensured, ensuring excellent controlled release properties.

When the polar term $\delta_{p,compound}$ and the hydrogen bonding term $\delta_{h,compound}$ of the antibiotic compound is within the above-described range, and the polar term $\delta_{p,polymer}$ and the hydrogen bonding term $\delta_{h,polymer}$ of the polymer are within the above-described range, the antibiotic compound is defined as being miscible with (dissolved in) the polymer without leaking from the suspension particles during radical polymerization.

In the method for producing controlled release particles of the present invention, first, the above-described hydrophobic antibiotic compound is dissolved in a hydrophobic polymerizable vinyl monomer without the presence of a solvent, thereby preparing a hydrophobic solution.

The hydrophobic solution can be obtained by blending the antibiotic compound and the polymerizable vinyl monomer without blending a solvent (hydrophobic organic solvents such as hexane, toluene, and ethyl acetate), and stirring the mixture homogeneously.

The mixing ratio of the antibiotic compound relative to the polymerizable vinyl monomer is, on a weight basis (that is, parts by weight of the antibiotic compound/parts by weight of the polymerizable vinyl monomer), for example, 10/90 to 60/40 (that is, 0.11 to 1.5).

In particular, when the antibiotic compound is liquid at normal temperature (20 to 30° C., to be more specific, 25° C.), the mixing ratio of the antibiotic compound relative to the polymerizable vinyl monomer is, because the antibiotic compound works as a plasticizer to the polymer of the polymerizable vinyl monomer, for example, 1/99 to 60/40, preferably 5/95 to 50/50 on a weight basis.

When the antibiotic compound is solid at normal temperature, because the controlled-release speed decreases compared with the case where the antibiotic compound is liquid at normal temperature, the mixing ratio of the antibiotic compound relative to the polymerizable vinyl monomer is, for example, 10/90 to 70/30, preferably 10/90 to 60/40 on a weight basis.

Preparation of the hydrophobic solution may be performed, for example, at normal temperature, or as necessary, can be performed by heating.

The heating temperature is, for example, 30 to 100° C., preferably 40 to 80° C.

Next, the hydrophobic solution is dispersed (suspended) in water.

That is, the hydrophobic solution and water is blended, and the mixture is stirred homogeneously, thereby allowing the hydrophobic solution to be dispersed (suspended) in water. A water dispersion (suspension) liquid of the hydrophobic solution is obtained in this manner.

Conditions for the dispersion in water are not particularly limited. For example, the dispersion in water may be performed at normal temperature, or can be performed by heating. Preferably, when heating is carried out at preparation of the hydrophobic solution, heating is carried out also at the time of dispersing in water. The heating temperature is, for example, the heating temperature of the above-described dispersion in water or more, to be specific, 30 to 100° C., preferably 40 to 80° C.

The mixing ratio of the water relative to 100 parts by weight of the hydrophobic solution is, for example, 100 to 1000 parts by weight, preferably 150 to 500 parts by weight.

When the hydrophobic solution is dispersed in water, preferably, a dispersing agent and a surfactant are blended.

Examples of dispersing agents include water-soluble polymers such as polyvinyl alcohol (PVA), polyvinyl pyrrolidone, gelatin, gum arabic, hydroxyethyl cellulose, hydroxypropyl cellulose, carboxymethyl cellulose, cationized starch, polyacrylic acid and its sodium salt, and styrene maleic acid copolymer and its sodium salt; and inorganic dispersing agents such as tribasic calcium phosphate, colloidal silica, monmorillinite, magnesium carbonate, aluminum hydroxide, and zinc white.

Of the dispersing agents, preferably, polyvinyl alcohol (PVA) or tribasic calcium phosphate is used.

The mixing ratio of the dispersing agent relative to 100 parts by weight of the hydrophobic solution is, for example, 0.01 to 10 parts by weight, preferably 0.1 to 5 parts by weight.

A surfactant is used preferably in combination with the above-described dispersing agent to effectively prevent aggregation of the particles during radical polymerization. Specific examples of surfactants include anionic surfactants such as sodium dodecylbenzenesulfonate, sodium lauryl sulfate, sodium di-2-ethylhexyl sulfosuccinate, sodium dodecyl diphenyl ether disulphonate, sodium nonyl diphenyl ether sulfonate, and naphthalenesulfonic acid formaldehyde condensate sodium salt; and non-ionic surfactants such as polyoxyethylene lauryl ether, polyoxyethylenenonylphenylether, polyoxyethylene monostearate, polyoxyethylene sorbitan monooleate, and polyoxyethylene polyoxypropylene block copolymer. Preferably, anionic surfactants are used.

The mixing ratio of the surfactant relative to 100 parts by weight of the hydrophobic solution is, for example, 0.0001 to 1.0 parts by weight, preferably 0.001 to 0.1 parts by weight.

These dispersing agents and surfactants can be blended, for example, before or after the blending of the hydrophobic solution with water, and preferably, these dispersing agents and surfactants are blended in water before being blended with the hydrophobic solution. An aqueous solution of the dispersing agent and the surfactant are prepared in this manner.

For the above-described dispersion (suspension) of the hydrophobic solution in water, for example, dispersers such as a homomixer, an ultrasonic homogenizer, a pressurized homogenizer, Milder, and a porous membrane injection disperser is used. Preferably, a homomixer is used.

Then, the polymerizable vinyl monomer in the hydrophobic solution dispersed in water is allowed to undergo radical polymerization in the presence of an oil-soluble initiator, thereby producing a polymer.

Examples of oil-soluble initiators include organic peroxides such as dilauroyl peroxide, 1,1,3,3-tetramethylbutylperoxy-2-ethylhexanoate, t-hexylperoxy-2-ethylhexanoate, diisopropylperoxydicarbonate, and benzoyl peroxide; and azo compounds such as 2,2'-azobisisobutyronitrile, 2,2'-azobis(2,4-dimethylvaleronitrile), and 2,2'-azobis(2-methylbutyronitrile).

The oil-soluble initiator can be blended, for example, in the hydrophobic solution before blended with water, or can be blended in the water dispersion liquid in which the hydrophobic solution is blended. Preferably, the oil-soluble initiator is blended in the hydrophobic solution before blended with water, to be more specific, in the hydrophobic solution right before blended with water.

The mixing ratio of the oil-soluble initiator relative to 100 parts by weight of the polymerizable vinyl monomer is, for example, 0.01 to 2 parts by weight, preferably 0.1 to 1 parts by weight.

This radical polymerization is suspension polymerization, because it is performed while stirring the suspension liquid to maintain the suspension state of the suspension liquid. Furthermore, because the ingredient monomer is only in the hydrophobic phase (oil phase), it is called in-situ polymerization.

In radical polymerization, reaction is initiated by heating, for example, the water dispersion liquid.

The heating conditions are appropriately selected depending on the kind of the oil-soluble initiator: the heating temperature is, for example, 30 to 100° C., preferably 50 to 100° C.; and the heating time is, for example, 3 to 24 hours, preferably 5 to 12 hours. Furthermore, the heating can also be carried out in stages: after heating to a predetermined temperature, the temperature is kept for a predetermined time period, and thereafter, the heating and the temperature keeping is repeated.

The pressure at the time of radical polymerization is not particularly limited, and radical polymerization is carried out at normal pressure.

Although radical polymerization is performed at normal pressure in the description above, the radical polymerization can also be performed at, for example, at high pressure. The high pressure allows the temperature in the reaction system to be set to a temperature exceeding 100° C., and also an antibiotic compound that is solid at room temperature can be easily made into liquid.

During radical polymerization, the polymer of the polymerizable vinyl monomer is preferably miscible with the antibiotic compound. That is, the polymer is dissolved in the antibiotic compound, forming a solution of the polymer in the antibiotic compound, and such an antibiotic compound solution is dispersed in water.

Because the polymerizable vinyl monomer is selected so that preferably, the combination of the above-described polymer of the polymerizable vinyl monomer and the antibiotic compound are miscible with each other at the polymerization temperature (heating temperature) during the above-described radical polymerization, phase separation during the radical polymerization (suspension polymerization) is prevented, and polymer (polymer during the reaction) dissolves the antibiotic compound, or the reaction advances in a state where the polymer (polymer during the reaction) is swollen with the antibiotic compound. Therefore, controlled-release particles with homogeneous phases formed can be obtained. When the antibiotic compound is liquid at normal temperature, the homogeneous state phase is kept as is also at normal temperature.

Thereafter, the temperature of the water dispersion liquid after polymerization is decreased, for example, by allowing the water dispersion liquid after polymerization to stand to cool.

The cooling temperature is, for example, room temperature (20 to 30° C., to be more specific, 25° C.).

After the cooling, the antibiotic compound is miscible within the polymer of the polymerizable vinyl monomer when the antibiotic compound is liquid at room temperature.

Similarly, when the antibiotic compound is solid at room temperature, after the cooling, the miscible state of the antibiotic compound is frozen, and dispersed as undetectably tiny solid microparticles in the particles of the polymer of the polymerizable vinyl monomer.

When the controlled release particles are formulated into powder formulation (described later) or granular formulation (described later), to prevent the controlled release particles to adhere to each other, the polymerizable vinyl monomer is selected so that the controlled release particles are preferably in a hard glass-state at room temperature.

The particle size of the controlled release particles is not particularly limited, and its average particle size (median size) is, for example, 500 nm to 1 mm, preferably 1 μm to 100 μm.

In particular, the average particle size of controlled release particles obtained from an antibiotic compound that is liquid at normal temperature is, for example, 5 to 100 μm, and the average particle size of the controlled release particles obtained from an antibiotic compound that is solid at normal temperature is, for example, 0.5 to 30 μm.

The water dispersion (suspension) liquid in which the controlled release particles with the antibiotic compound homogeneously present therein are dispersed (suspended) in water can be obtained in this manner.

Then, to the water dispersion (suspension) liquid containing the controlled release particles, as necessary, known additives such as another dispersing agent, a thickening agent, an antifreezing agent, an antiseptic, a microbial growth inhibitor, and a specific gravity adjuster are blended appropriately.

The thus obtained controlled release particles may be used as is (water dispersion liquid or suspension liquid), that is, may be used as water dispersion formulation or suspension formulation, or for example, may be formulated into a known form such as powder formulation or granular formulation, after solid-liquid separation by filtration and/or centrifugal separation, etc. and used. As necessary, the controlled release particles can be washed with water and/or acid. Furthermore, the water dispersion (suspension) liquid can be dried by spraying or by air as is, to be formulated into forms such as powder formulation or granular formulation.

Powder formulation is excellent in flowability particularly when tribasic calcium phosphate is used as the dispersing agent. By dispersing or suspending the powder formulation in water again, water dispersion formulation or suspension formulation can be prepared again. Thus, the powder formulation is excellent in re-dispersibility in water or forming re-suspension.

Thus, by preparing the controlled release particles as powder formulation at the time of transportation, and preparing (re-formulation, reproduction) the powder formulation again as water dispersion or suspension, the transportation costs can be reduced, and furthermore, its application can be expanded.

Furthermore, in the present invention, despite the low melting point of 100° C. or less of the antibiotic compound, the controlled release particles containing the antibiotic compound, particularly the powder formulation of the controlled release particles is excellent in handleability.

With the above-described method for producing controlled release particles of the present invention, a polymer having a polar term $\delta_{p,polymer}$ and a hydrogen bonding term $\delta_{h,polymer}$ of the solubility parameter ($\delta$) in predetermined ranges is produced by polymerizing a hydrophobic polymerizable monomer in which an antibiotic compound is dissolved and having a polar term $\delta_{p,compound}$ and a hydrogen bonding term $\delta_{h,compound}$ of the solubility parameter ($\delta$) in predetermined ranges, and therefore preparation of ingredients are made easy, production steps are made simple, and furthermore, ingredients costs are reduced, allowing reduction in production costs.

Therefore, controlled release particles having excellent controlled release properties and capable of exhibiting excellent lasting effects can be obtained easily and at low cost.

Therefore, the controlled release particles can be applied to various industrial products, for example, indoor/outdoor paint, rubber, fiber, resin, plastic, adhesive, joint mixture, sealing agent, building material, caulking agent, soil treating agent, lumber, white water in paper-making processes, pigment, treatment liquid for printing plates, cooling water, ink, cutting oil, cosmetic products, nonwoven fabric, spinning oil, and leather. The amount of the antibiotic compound blended in the controlled release particles for these industrial products is, for example, 10 to 100000 mg/kg (product weight).

Furthermore, with the above-described method, the hydrophobic solution is prepared without using a solvent, and therefore environmental burden can be reduced.

Thus, the controlled release particles can be suitably blended in outdoor/indoor water-based paint. Examples of water-based paint include paints using emulsion or aqueous resin of acrylic, acrylic-styrene, styrene, vinyl acetate, vinyl acetate-acrylic, polyester, silicone, urethane, alkyd, and fluorine resin, or mixtures thereof as a vehicle. In particular, when the controlled release particles are blended in a zero VOC paint, environmental burden can be reduced, and stability of the controlled release particles can be kept excellently, and further improvement in lasting effects can be achieved.

EXAMPLES

Details of the abbreviations used in Examples and Comparative Examples are shown below.

IPBC: trade name "Fungitrol 400", 3-iodo-2-propynylbutyl-carbamate, molecular weight 281, melting point: 60° C., water solubility: 150 ppm, polar term $\delta_{p,compound}$ of solubility parameter ($\delta$): 3.23 [(J/cm$^3$)$^{1/2}$], hydrogen bonding term $\delta_{h,compound}$ of solubility parameter ($\delta$): 7.83 [(J/cm$^3$)$^{1/2}$], manufactured by International Specialty Products Inc.

OIT: trade name "KATHON 893T" ("KATHON" is a registered trademark), 2-n-octyl-4-isothiazoline-3-one, molecular weight 213, melting point: below 20° C., water solubility: 300 ppm, polar term $\delta_{p,compound}$ of solubility parameter ($\delta$): 5.47 [(J/cm$^3$)$^{1/2}$], hydrogen bonding term $\delta_{h,compound}$ of solubility parameter ($\delta$): 5.87 [(J/cm$^3$)$^{1/2}$], manufactured by Rohm and Haas Company Cyfluthrin: trade name "Preventol HS12" ("Preventol" is registered trademark), (RS)-α-cyano-4-fluoro-3-phenoxybenzyl-(1RS,3RS)-(1RS,3RS)-3-(2,2-dichlorovinyl)-2,2-methylcyclopropane carboxylate, molecular weight 434, water solubility: 1 to 2 ppb, mixture of isomer I (melting point 57° C.), isomer II (melting point 74° C.), isomer III (melting point 66° C.), and isomer IV (melting point 102° C.), polar term $\delta_{p,compound}$ of solubility parameter ($\delta$): 3.46 [(J/cm$^3$)$^{1/2}$], hydrogen bonding term $\delta_{h,compound}$ of solubility parameter ($\delta$): 6.09 [(J/cm$^3$)$^{1/2}$], manufactured by LANXESS Propiconazole: 1-[2-(2,4-dichlorophenyl)-4-n-propyl-1,3-dioxolane-2-ylmethyl]-1H-1,2,4-triazole, molecular weight 342, melting point: below 20° C., water solubility: 110 ppm, polar term $\delta_{p,compound}$ of solubility parameter ($\delta$): 6.55 [(J/cm$^3$)$^{1/2}$], hydrogen bonding term $\delta_{h,compound}$ of solubility parameter ($\delta$): 9.44 [(J/cm$^3$)$^{1/2}$], manufactured by HAKKO TSUSHO CO., LTD.

Prochloraz: N-propyl-N-[2-(2,4,6-trichloro-phenoxy)ethyl] imidazole-1-carboxamide, molecular weight 375, melting point 45 to 52° C., water solubility: 55 ppm, polar term $\delta_{p,compound}$ of solubility parameter ($\delta$): 7.07 [(J/cm$^3$)$^{1/2}$], hydrogen bonding term $\delta_{h,compound}$ of solubility parameter ($\delta$): 8.31 [(J/cm$^3$)$^{1/2}$], manufactured by Maruzen Chemicals Co., Ltd.
Flusilazole: bis(4-fluorophenyl)methyl (1H-1,2,4-triazole-1-ylmethylsliane, molecular weight 315, melting point: 54° C., water solubility: 45 ppm, polar term $\delta_{p,compound}$ of solubility parameter ($\delta$): 5.95 [(J/cm$^3$)$^{1/2}$], hydrogen bonding term $\delta_{h,compound}$ of solubility parameter ($\delta$): 6.85 [(J/cm$^3$)$^{1/2}$], manufactured by ARBROWN CO., LTD.
MBACT: trade name "Irgarol 1071" ("Irgarol" is a registered trademark), 2-methylthio-4-t-butylamino-6-cyclopropylamino-s-triazine, molecular weight 253, melting point: 133° C., water solubility: 7 ppm, polar term $\delta_{p,compound}$ of solubility parameter ($\delta$): 7.18 [(J/cm$^3$)$^{1/2}$], hydrogen bonding term $\delta_{h,compound}$ of solubility parameter ($\delta$): 8.77 [(J/cm$^3$)$^{1/2}$], manufactured by Ciba Specialty Chemicals Inc.
Capric acid: molecular weight 172, melting point: 29 to 32° C., water solubility: 1.5 wt %, polar term $\delta_{p,monomer\ unit}$ of solubility parameter ($\delta$): 2.20 [(J/cm$^3$)$^{1/2}$], hydrogen bonding term $\delta_{h,monomer\ unit}$ of solubility parameter ($\delta$): 7.24 [(J/cm$^3$)$^{1/2}$].
Methyl methacrylate: trade name "ACRYESTER M", water solubility: 1.6 wt %, polar term $\delta_{p,monomer\ unit}$ of solubility parameter ($\delta$) as monomer unit: 5.98 [(J/cm$^3$)$^{1/2}$], hydrogen bonding term $\delta_{h,monomer\ unit}$ of solubility parameter ($\delta$) as monomer unit: 9.25 [(J/cm$^3$)$^{1/2}$], manufactured by Mitsubishi Rayon Co., Ltd.
n-Butyl methacrylate: water solubility: 0.08 wt %, polar term $\delta_{p,monomer\ unit}$ of solubility parameter ($\delta$) as monomer unit: 3.76 (J/cm$^3$)$^{1/2}$], hydrogen bonding term $\delta_{h,monomer\ unit}$ of solubility parameter ($\delta$) as monomer unit: 7.33 [(J/cm$^3$)$^{1/2}$], manufactured by Mitsubishi Rayon Co., Ltd.
Methyl acrylate: water solubility: 5.7 wt %, polar term $\delta_{p,monomer\ unit}$ of solubility parameter ($\delta$) as monomer unit: 7.36 [(J/cm$^3$)$^{1/2}$], hydrogen bonding term $\delta_{h,monomer\ unit}$ of solubility parameter ($\delta$) as monomer unit: 10.25 [(J/cm$^3$)$^{1/2}$], manufactured by Nippon Shokubai Co., Ltd.
Ethyl acrylate: water solubility: 1.5 wt %, polar term $\delta_{p,monomer\ unit}$ of solubility parameter ($\delta$) as monomer unit: 5.93 [(J/cm$^3$)$^{1/2}$], hydrogen bonding term $\delta_{h,monomer\ unit}$ of solubility parameter ($\delta$) as monomer unit: 9.20 [(J/cm$^3$)$^{1/2}$], manufactured by Nippon Shokubai Co., Ltd.
n-Butyl acrylate: water solubility: 0.2 wt %, polar term $\delta_{p,monomer\ unit}$ of solubility parameter ($\delta$) as monomer unit: 4.26[(j/cm$^3$)$^{1/2}$], hydrogen bonding term $\delta_{h,monomer\ unit}$ of solubility parameter ($\delta$) as monomer unit: 7.81 [(J/cm$^3$)$^{1/2}$], manufactured by Nippon Shokubai Co., Ltd.
Methacrylic acid: water solubility: 8.9 wt %, polar term $\delta_{p,monomer\ unit}$ of solubility parameter ($\delta$) as monomer unit: 7.13 [(J/cm$^3$)$^{1/2}$], hydrogen bonding term $\delta_{h,monomer\ unit}$ of solubility parameter ($\delta$) as monomer unit: 13.03 [(J/cm$^3$)$^{1/2}$], manufactured by Mitsubishi Rayon Co., Ltd.
Styrene: water-insoluble, polar term $\delta_{p,monomer\ unit}$ of solubility parameter ($\delta$) as monomer unit: 1.27 [(J/cm$^3$)$^{1/2}$], hydrogen bonding term $\delta_{h,monomer\ unit}$ of solubility parameter ($\delta$) as monomer unit: 0.00 [(J/cm$^3$)$^{1/2}$].
Ethylene glycol dimethacrylate: trade name "Light Ester EG", water-insoluble, polar term $\delta_{p,monomer\ unit}$ of solubility parameter ($\delta$) as monomer unit: 5.37 [(J/cm$^3$)$^{1/2}$], hydrogen bonding term $\delta_{h,monomer}$ of solubility parameter ($\delta$) as monomer unit: 10.42 [(J/cm$^3$)$^{1/2}$], manufactured by Kyoeisha Chemical Co., Ltd.
Trimethylolpropanetrimethacrylate: trade name "Light Ester TMP", water-insoluble, polar term $\delta_{p,monomer\ unit}$ of solubility parameter ($\delta$): 3.79 [(J/cm$^3$)$^{1/2}$], hydrogen bonding term $\delta_{h,monomer\ unit}$ of solubility parameter ($\delta$): 9.68 [(J/cm$^3$)$^{1/2}$], manufactured by Kyoeisha Chemical Co., Ltd Dilauroyl peroxide: trade name "PEROYL® L" ("PEROYL" is registered trademark), manufactured by NOF CORPORATION
PVA-217: trade name "Kuraray Poval 217", partially saponified polyvinyl alcohol, manufactured by Kuraray Co., Ltd.
TCP-10U: trade name, a suspension liquid of 10 wt % tribasic calcium phosphate
(3 [Ca$_3$(PO$_4$)$_2$].Ca(OH)$_2$) in water, manufactured by Matsuo Yakuhin Sangyo K. K.
DBN: trade name "NEOPELEX No. 6 powder" ("NEOPELEX" is registered trademark), sodium dodecylbenzene sulphonate, manufactured by Kao Corporation
Pelex SS-L: trade name ("Pelex" is registered trademark), sodium dodecyl diphenyl ether disulphonate, manufactured by Kao Corporation Example 1

Formulation of Suspension Containing IPBC-containing Controlled Release Particles A 200 mL beaker (1) was charged with 40 g of IPBC, 54 g of methyl methacrylate, 6 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of a solution of 10% PVA-217 in water, and 200 mg of a solution of 5% DBN in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation) at a number of revolution of 5000 rpm for 10 min, thereby dispersing the hydrophobic solution in water, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature.

In the suspension polymerization, the polymerization was regarded as started at the point where the temperature reached 55° C., and thereafter, the polymerization was performed continuously at 60±2° C. for 1 hour, at 70±2° C. for 3 hours, and at 80±2° C. for 2 hours.

Thereafter, the reacted suspension liquid was cooled to 30° C. or less, thereby producing a suspension liquid (suspension) of controlled release particles containing IPBC and having a median size of 7.4 µm.

The median size of the controlled release particles was measured with a laser diffraction scattering particle size distribution analyzer LA-920 (manufactured by HORIBA, Ltd.). The median size was measured in the same manner in the following Examples and Comparative Examples as well.

Example 2

Formulation of Suspension containing IPBC-containing Controlled Release Particles A 200 mL beaker (1) was charged with 40 g of IPBC, 42 g of methyl methacrylate, 18 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of TCP-10U, and 200 mg of a 5% solution of Pelex SS-L in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation) at a number of revolution of 5000 rpm for 10 min, thereby dispersing the hydrophobic solution in water, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature.

In the suspension polymerization, the polymerization was regarded as started at the point where the temperature reached 55° C., and thereafter, the polymerization was performed continuously at 60±2° C. for 1 hour, at 70±2° C. for 3 hours, and at 80±2° C. for 2 hours.

Thereafter, the reacted suspension liquid was cooled to 30° C. or less, thereby producing a suspension liquid (suspension) of controlled release particles containing IPBC and having a median size of 8.2 µm.

Example 3

Formulation of Suspension Containing IPBC-containing Controlled Release Particles A suspension liquid (suspension) of controlled release particles containing IPBC and having a median size of 9.6 µm was obtained by dispersing a hydrophobic solution in water, and then performing suspension polymerization in the same manner as in Example 1, except that the amounts of methyl methacrylate and ethylene glycol dimethacrylate charged were changed to 30 g.

Example 4

Formulation of Suspension Containing OIT-Containing Controlled Release Particles A 200 mL beaker (1) was charged with 40 g of OIT, 54 g of methyl methacrylate, 6 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of a solution of 10% PVA-217 in water, and 200 mg of 5% DBN in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation) at a number of revolution of 2000 rpm for 10 min, thereby dispersing the hydrophobic solution in water, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature.

In the suspension polymerization, the polymerization was regarded as started at the point where the temperature reached 55° C., and thereafter, the polymerization was performed continuously at 60±2° C. for 2 hours, at 70±2° C. for 2 hours, and at 80±2° C. for 3 hours.

Thereafter, the reacted suspension liquid was cooled to 30° C. or less, thereby producing a suspension liquid (suspension) of controlled release particles containing OIT and having a median size of 14 µm.

Example 5

Formulation of Suspension Containing OIT-Containing Controlled Release Particles A suspension liquid (suspension) of controlled release particles containing OIT and having a median size of 14 µm was obtained by dispersing a hydrophobic solution in water, and then performing suspension polymerization in the same manner as in Example 4, except that the amounts of methyl methacrylate and ethylene glycol dimethacrylate were changed to 30 g.

Example 6

Formulation of Suspension Containing OIT-Containing Controlled Release Particles A suspension liquid (suspension) of controlled release particles containing OIT and having a median size of 9.8 µm was obtained by dispersing a hydrophobic solution in water and then performing suspension polymerization in the same manner as in Example 4, except that the amounts of OIT, methyl methacrylate, and ethylene glycol dimethacrylate were changed to 50 g, 45 g, and 5 g, respectively.

Example 7

Formulation of Suspension Containing OIT-Containing Controlled Release Particles A suspension liquid (suspension) of controlled release particles containing IPBC and having a median size of 29 µm was obtained by dispersing a hydrophobic solution in water, and then performing suspension polymerization in the same manner as in Example 4, except that the number of revolution in the conditions of stirring with T.K. Homo Mixer MARK Model 2.5 (manufactured by PRIMIX Corporation) at the time of dispersing in water were changed to 1000 rpm.

Example 8

Formulation of Suspension Containing Cyfluthrin-Containing Microparticles

A 200 mL beaker (1) was charged with 40 g of cyfluthrin, 54 g of methyl methacrylate, 6 g of trimethylolpropanetrimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of a 10% solution of PVA-217 in water, and 200 mg of a 5% solution of DBN in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation)

at a number of revolution of 3000 rpm for 10 mm, thereby dispersing the hydrophobic solution in water, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature.

In the suspension polymerization, the polymerization was regarded as started at the point where the temperature reached 55° C., and thereafter, the polymerization was performed continuously at 60±2° C. for 2 hours, at 70±2° C. for 2 hours, and at 80±2° C. for 2 hours.

Thereafter, the reacted suspension liquid was cooled to 30° C. or less, thereby producing a suspension liquid (suspension) of controlled release particles containing cyfluthrin and having a median size of 15 μm.

Example 9

Formulation of Suspension Containing OIT-Containing Controlled Release Particles A 200 mL beaker (1) was charged with 40 g of OIT, 36 g of methyl methacrylate, 6 g of methacrylic acid, 18 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of TCP-10U, and 200 mg of a 5% solution of Pelex SS-L in water, and then the mixture was stirred at room temperature, thereby producing a homogeneous aqueous solution.

Then, the hydrophobic solution was added to the 500 mL beaker (2), and the mixture was stirred with T.K.Homo Mixer MARK Model 2.5 (manufactured by PRIMIX Corporation) at 2000 rpm for 10 min, thereby dispersing the hydrophobic solution in water, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature.

In the suspension polymerization, the polymerization was regarded as started at the point where the temperature reached 55° C., and thereafter, the polymerization was performed at 60±2° C. for 2 hours, at 70±2° C. for 2 hours, and at 80±2° C. for 2 hours.

Thereafter, the reacted suspension liquid was cooled to 30° C. or less, thereby producing a suspension liquid (suspension) of controlled release particles containing OIT and having a median size of 36 μm.

Example 10

Formulation of Suspension Containing Cyfluthrin-Containing Controlled Release Particles A 200 mL beaker (1) was charged with 40 g of cyfluthrin, 42 g of methyl methacrylate, 18 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of TCP-10U, and 200 mg of a 5% solution of Pelex SS-L in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation) at 3000 rpm for 10 min, thereby dispersing the hydrophobic solution in water, and preparing a suspension liquid.

Thereafter, the suspension liquid was transferred to a 500 mL, 4-neck flask equipped with a stirrer and a reflux condenser, and subjected to suspension polymerization under nitrogen gas current, while stirring and increasing the temperature.

In the suspension polymerization, the polymerization was regarded as started at the point where the temperature reached 55° C., and thereafter, the polymerization was performed continuously at 60±2° C. for 2 hours, at 70±2° C. for 2 hours, and at 80±2° C. for 2 hours.

Thereafter, the reacted suspension liquid was cooled to 30° C. or less, thereby producing a suspension liquid (suspension) of controlled release particles containing cyfluthrin (mixture of isomer I, isomer II, and isomer III) and having a median size of 22 μm.

Example 11

Formulation of Suspension Containing Propiconazole-Containing Controlled Release Particles A suspension liquid (suspension) of controlled release particles containing propiconazole and having a median size of 19 μm was obtained by dispersing a hydrophobic solution in water and then performing suspension polymerization in the same manner as in Example 10, except that 40 g of propiconazole was charged instead of 40 g of cyfluthrin.

Example 12

Formulation of Suspension Containing Prochloraz-Containing Controlled Release Particles A suspension liquid (suspension) of controlled release particles containing prochloraz and having a median size of 30 μm was obtained by dispersing a hydrophobic solution in water and then performing suspension polymerization in the same manner as in Example 10, except that 40 g of prochloraz was charged instead of 40 g of cyfluthrin.

Example 13

Formulation of Suspension Containing Flusilazole-Containing Controlled Release Particles A suspension liquid (suspension) of controlled release particles containing flusilazole and having a median size of 32 μm was obtained by dispersing a hydrophobic solution in water and then performing suspension polymerization in the same manner as in Example 10, except that 40 g of flusilazole was charged instead of 40 g of cyfluthrin.

Example 14

Formulation of Suspension Containing IPBC-Containing Controlled Release Particles A 200 mL beaker (1) was charged with 40 g of IPBC, 24 g of methyl methacrylate, 18 g of n-butyl methacrylate, 18 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of a 10% solution of PVA-217 in water, and 200 mg of a 5% solution of DBN in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation) at 3000 rpm for 10 min, thereby dispersing the hydrophobic solution in water, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature.

In the suspension polymerization, the polymerization was regarded as started at the point where the temperature reached 55° C., and thereafter, the polymerization was performed continuously at 60±2° C. for 1 hour, 70±2° C. for 3 hours, and 80±2° C. for 2 hours.

Thereafter, the reacted suspension liquid was cooled to 30° C. or less, thereby producing a suspension liquid (suspension) of controlled release particles containing IPBC and having a median size of 24 μm.

Example 15

Formulation of Suspension Containing IPBC-Containing Controlled Release Particles A suspension liquid (suspension) of controlled release particles containing IPBC and having a median size of 22 μm was obtained by dispersing a hydrophobic solution in water and then performing suspension polymerization in the same manner as in Example 14, except that 18 g of ethyl acrylate was charged instead of 18 g of n-butyl methacrylate.

Example 16

Formulation of Suspension Containing IPBC-Containing Controlled Release Particles A suspension liquid (suspension) of controlled release particles containing IPBC and having a median size of 22 μm was obtained by dispersing a hydrophobic solution in water and then performing suspension polymerization in the same manner as in Example 14, except that 18 g of n-butyl acrylate was charged instead of 18 g of n-butyl methacrylate.

Comparative Example 1

Formulation of Suspension Containing MBACT-Containing Controlled Release Particles A 200 mL beaker (1) was charged with 10 g of MBACT, 81 g of methyl methacrylate, 9 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of a 10% solution of PVA-217 in water, and 200 mg of a 5% solution of DBN in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation) at a number of revolution of 3000 rpm for 10 min, thereby dispersing the hydrophobic solution in water, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature.

In the suspension polymerization, the polymerization was regarded as started at the point where the temperature reached 55° C., and thereafter, the polymerization was performed continuously at 60±2° C. for 2 hours, 70±2° C. for 3 hours, and 80±2° C. for 2 hours.

Thereafter, the reacted suspension liquid was cooled to 30° C. or less, thereby producing a suspension liquid (suspension) of controlled release particles containing MBACT and having a median size of 20 μm.

Comparative Example 2

Formulation of Suspension Containing MBACT-Coexisting Particles

A 200 mL beaker (1) was charged with 40 g of MBACT, 54 g of methyl methacrylate, and 6 g of ethylene glycol dimethacrylate, and the temperature was increased while the mixture was stirred, thereby preparing a homogeneous hydrophobic solution having a temperature of 70° C.

Separately, a 500 mL beaker (2) was charged with 280 g of ion-exchange water, 20 g of a 10% solution of PVA-217 in water, and 200 mg of a 5% solution of DBN in water, and the temperature was increased while the mixture was stirred, thereby preparing a homogeneous aqueous solution having a temperature of 70° C.

Then, after 300 mg of dilauroyl peroxide was added to a 200 mL beaker (1), this monomer solution was immediately added to a beaker (2), and while keeping the liquid temperature of 70° C., the mixture was stirred with T.K. Homo Mixer MARK Model 2.5 (manufactured by PRIMIX Corporation) at a number of revolution of 3000 rpm for 10 min, thereby dispersing the hydrophobic solution in water, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature.

In the suspension polymerization, the polymerization was performed continuously at 70±2° C. for 5 hours, and 80±2° C. for 2 hours.

Thereafter, the reacted suspension liquid was cooled to 30° C. or less, thereby producing a suspension liquid (suspension) of particles where MBACT coexists and having a median size of 26 μm.

Comparative Example 3

Formulation of Suspension Containing Capric Acid-Containing Controlled Release Particles A 200 mL beaker (1) was charged with 40 g of capric acid, 42 g of methyl methacrylate, 18 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of TCP-10U and 200 mg of a 5% solution of Pelex SS-L in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation) at 2000 rpm for 10 min, thereby dispersing the hydrophobic solution in water, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature.

In the suspension polymerization, the polymerization was regarded as started at the point where the temperature reached 55° C., and thereafter, the polymerization was performed continuously at 60±2° C. for 1 hour, 70±2° C. for 2 hours, and 80±2° C. for 2 hours.

Thereafter, as the reacted suspension liquid was cooled to 30° C. or less, capric acid dissolved in the aqueous phase deposited and the suspension liquid solidified, and thus a suspension could not be prepared.

Comparative Example 4

Formulation of Suspension Containing IPBC-Coexisting Particles

A 200 mL beaker (1) was charged with 40 g of IPBC, 42 g of n-butyl methacrylate, 18 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of a 10% solution of PVA-217 in water, and 200 mg of a 5% solution of DBN in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation) at a number of revolution of 3000 rpm for 10 min, thereby dispersing the hydrophobic solution in water, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature.

In the suspension polymerization, the polymerization was regarded as started at the point where the temperature reached 55° C., and thereafter, the polymerization was performed continuously at 60±2° C. for 1 hour, 70±2° C. for 3 hours, and 80±2° C. for 2 hours.

Thereafter, the reacted suspension liquid was cooled to 30° C. or less, thereby producing a suspension liquid (suspension) of particles where IPBC coexists and having a median size of 28 μm.

Comparative Example 5

Formulation of Suspension Containing IPBC-Coexisting Particles

A suspension liquid (suspension) of particles where IPBC coexist and having a median size of 30 μm was obtained by performing suspension polymerization in the same manner as in Example 2, except that 42 g of styrene was charged instead of 42 g of methyl methacrylate, and the number of revolution of the Homo Mixer was changed to 3000 rpm when the hydrophobic solution was dispersed in water.

Comparative Example 6

Formulation of Suspension Containing IPBC-Coexisting Particles

A suspension liquid (suspension) of particles where IPBC coexists and having a median size of 11 μm was obtained by dispersing a hydrophobic solution in water and then performing suspension polymerization in the same manner as in Comparative Example 4, except that 42 g of methyl acrylate was charged instead of 42 g of n-butyl methacrylate.

Formulation of components in Examples and Comparative Examples is shown in Table 2 to Table 4. In the tables, values of the mixing formulation are shown in grams (solid content except for ion-exchange water).

TABLE 2

| | | | | | Examples and Comparative Examples | | | | | | | |
|---|---|---|---|---|---|---|---|---|---|---|---|---|
| | | | | | Ex. 1 | Ex. 2 | Ex. 3 | Ex. 4 | Ex. 5 | Ex. 6 | Ex. 7 | Ex. 8 |
| | | | Molecular-weight | Melting Point(° C.) | | | | | | | | |
| Hydrophobic Solution | Antibiotic compound | IPBC | 281 | 60 | 40 | 40 | 40 | — | — | — | — | — |
| | | OIT | 213 | <20 | — | — | — | 40 | 40 | 50 | 40 | — |
| | | Cyfluthrin | 434 | 57, 74, 66*1 | — | — | — | — | — | — | — | 40 |
| | | Propiconazole | 342 | <20 | — | — | — | — | — | — | — | — |
| | | Prochloraz | 375 | 45 to 52 | — | — | — | — | — | — | — | — |
| | | Flusilazole | 315 | 54 | — | — | — | — | — | — | — | — |
| | | MBACT | 253 | 133 | — | — | — | — | — | — | — | — |
| | | Capric Acid*2 | 172 | 29 to 32 | — | — | — | — | — | — | — | — |
| | | Mixing Ratio of Antibiotic Compound relative to Polymerizable Vinyl monomer | | | 0.67 | 0.67 | 0.67 | 0.67 | 0.67 | 1.00 | 0.67 | 0.67 |
| | | Solubility Parameter δ [(J/cm$^3$)$^{1/2}$] | | Polar Term $\delta_{p, compound}$ | 3.23 | 3.23 | 3.23 | 5.47 | 5.47 | 5.47 | 5.47 | 3.46 |
| | | | | Hydrogen Bonding Term $\delta_{h, compound}$ | 7.83 | 7.83 | 7.83 | 5.87 | 5.87 | 5.87 | 5.87 | 6.09 |

TABLE 2-continued

| | | | Ex. 1 | Ex. 2 | Ex. 3 | Ex. 4 | Ex. 5 | Ex. 6 | Ex. 7 | Ex. 8 |
|---|---|---|---|---|---|---|---|---|---|---|
| Polymerizable vinyl monomer | Compatible Monomer | Methyl methacrylate | 54 | 42 | 30 | 54 | 30 | 45 | 54 | 54 |
| | | n-Butyl methacrylate | — | — | — | — | — | — | — | — |
| | | Methyl acrylate | — | — | — | — | — | — | — | — |
| | | Ethyl acrylate | — | — | — | — | — | — | — | — |
| | | n-Butyl acrylate | — | — | — | — | — | — | — | — |
| | | Methacrylic acid | — | — | — | — | — | — | — | — |
| | | Styrene | — | — | — | — | — | — | — | — |
| | Crosslinkable Monomer | Ethylene glycol dimethacrylate | 6 | 18 | 30 | 6 | 30 | 5 | 6 | — |
| | | Trimethylolpropane trimethacrylate | — | — | — | — | — | — | — | 6 |
| | Oil-soluble Initiator | Dilauroyl peroxide | 0.3 | 0.3 | 0.3 | 0.3 | 0.3 | 0.3 | 0.3 | 0.3 |
| | Ion-Exchange Water | | 280 | 280 | 280 | 280 | 280 | 280 | 280 | 280 |
| Polymer | Solubility Parameter δ [(J/cm³)^{1/2}] | Polar Term $\delta_{p, polymer}$ | 5.92 | 5.80 | 5.68 | 5.92 | 5.68 | 5.92 | 5.92 | 5.76 |
| | | Hydrogen Bonding Term $\delta_{h, polymer}$ | 9.36 | 9.60 | 9.83 | 9.36 | 9.83 | 9.36 | 9.36 | 9.29 |
| $\Delta\delta_p$ | $(=\delta_{p, polymer} - \delta_{p, compound})[(J/cm^3)^{1/2}]$ | | 2.69 | 2.57 | 2.45 | 0.45 | 0.21 | 0.45 | 0.45 | 2.30 |
| $\Delta\delta_h$ | $(=\delta_{h, polymer} - \delta_{h, compound})[(J/cm^3)^{1/2}]$ | | 1.53 | 1.77 | 2.00 | 3.49 | 3.96 | 3.49 | 3.49 | 3.20 |
| Dispersing Agent | | PVA-217 | 2 | — | 2 | 2 | 2 | 2 | 2 | 2 |
| | | TCP-10U | — | 2 | — | — | — | — | — | — |
| Surfactant | | DBN | 0.01 | — | 0.01 | 0.01 | 0.01 | 0.01 | 0.01 | 0.01 |
| | | Pelex SS-L | — | 0.01 | — | — | — | — | — | — |
| Concentration of Sustained Release Particles (wt %) [vs Suspension Liquid] | | | 25.5 | 25.5 | 25.5 | 25.5 | 25.5 | 25.5 | 25.5 | 25.5 |
| Concentration of Antibiotic Compound (wt %) [vs Suspension Liquid] | | | 10.0 | 10.0 | 10.0 | 10.0 | 10.0 | 12.5 | 10.0 | 10.0 |
| Stirring Conditions with Homo Mixer at the time of Water Dispersion | | Number of Revolution(rpm) | 5000 | 5000 | 5000 | 2000 | 2000 | 2000 | 1000 | 3000 |
| Median Size of Sustained Release Particles(μm) | | | 7.4 | 8.2 | 9.6 | 14 | 14 | 9.8 | 29 | 15 |

[1] containing Isomer IV(Melting Point102° C.)
[2] Hydrophilic

TABLE 3

| | | | | | Ex. 9 | Ex. 10 | Ex. 11 | Ex. 12 | Ex. 13 | Ex. 14 | Ex. 15 | Ex. 16 |
|---|---|---|---|---|---|---|---|---|---|---|---|---|
| | | | Molecular-weight | Melting Point(° C.) | | | | | | | | |
| Hydrophobic Solution | Antibiotic Compound | IPBC | 281 | 60 | — | — | — | — | — | 40 | 40 | 40 |
| | | OIT | 213 | <20 | 40 | — | — | — | — | — | — | — |
| | | Cyfluthrin | 434 | 57, 74, 66*[1] | — | 40 | — | — | — | — | — | — |
| | | Propiconazole | 342 | <20 | — | — | 40 | — | — | — | — | — |
| | | Prochloraz | 375 | 45 to 52 | — | — | — | 40 | — | — | — | — |
| | | Flusilazole | 315 | 54 | — | — | — | — | 40 | — | — | — |
| | | MBACT | 253 | 133 | — | — | — | — | — | — | — | — |
| | | Capric Acid*[2] | 172 | 29 to 32 | — | — | — | — | — | — | — | — |
| | Mixing Ratio of Antibiotic Compound relative to Polymerizable Vinyl monomer | | | | 0.67 | 0.67 | 0.67 | 0.67 | 0.67 | 0.67 | 0.67 | 0.67 |
| | Solubility Parameter δ [(J/cm³)^{1/2}] | Polar Term $\delta_{p, compound}$ | | | 5.47 | 3.46 | 6.55 | 7.07 | 5.95 | 3.23 | 3.23 | 3.23 |
| | | Hydrogen Bonding Term $\delta_{h, compound}$ | | | 5.87 | 6.09 | 9.44 | 8.31 | 6.85 | 7.83 | 7.83 | 7.83 |
| Polymerizable vinyl monomer | Compatible Monomer | Methyl methacrylate | | | 36 | 42 | 42 | 42 | 42 | 24 | 24 | 24 |
| | | n-Butyl methacrylate | | | — | — | — | — | — | 18 | — | — |
| | | Methyl acrylate | | | — | — | — | — | — | — | — | — |
| | | Ethyl acrylate | | | — | — | — | — | — | — | 18 | — |
| | | n-Butyl acrylate | | | — | — | — | — | — | — | — | 18 |
| | | Methacrylic acid | | | 6 | — | — | — | — | — | — | — |
| | | Styrene | | | — | — | — | — | — | — | — | — |
| | Crosslinkable Monomer | Ethylene glycol dimethacrylate | | | 18 | 18 | 18 | 18 | 18 | 18 | 18 | 18 |
| | | Trimethylolpropane trimethacrylate | | | — | — | — | — | — | — | — | — |
| | Oil-soluble Initiator | Dilauroyl peroxide | | | 0.3 | 0.3 | 0.3 | 0.3 | 0.3 | 0.3 | 0.3 | 0.3 |
| | Ion-Exchange Water | | | | 280 | 280 | 280 | 280 | 280 | 280 | 280 | 280 |

TABLE 3-continued

|  |  |  | Ex. 9 | Ex. 10 | Ex. 11 | Ex. 12 | Ex. 13 | Ex. 14 | Ex. 15 | Ex. 16 |
|---|---|---|---|---|---|---|---|---|---|---|
| Polymer | Solubility Parameter $\delta$ [(J/cm$^3$)$^{1/2}$] | Polar Term $\delta_{p, polymer}$ | 5.91 | 5.80 | 5.80 | 5.80 | 5.80 | 5.13 | 5.78 | 5.28 |
|  |  | Hydrogen Bonding Term $\delta_{h, polymer}$ | 9.98 | 9.60 | 9.60 | 9.60 | 9.60 | 9.02 | 9.58 | 9.16 |
| $\Delta\delta_p$ | (=$\delta_{p, polymer}$ − $\delta_{p, compound}$)[(J/cm$^3$)$^{1/2}$] |  | 0.44 | 0.33 | 2.34 | −1.27 | −0.15 | 1.90 | 2.55 | 2.05 |
| $\Delta\delta_h$ | (=$\delta_{h, polymer}$ − $\delta_{h, compound}$)[(J/cm$^3$)$^{1/2}$] |  | 4.11 | 3.73 | 3.51 | −1.29 | 2.75 | 1.19 | 1.75 | 1.33 |
| Dispersing Agent |  | PVA-217 | — | — | — | — | — | 2 | 2 | 2 |
|  |  | TCP-10U | 2 | 2 | 2 | 2 | 2 | — | — | — |
| Surfactant |  | DBN | — | — | — | — | — | 0.01 | 0.01 | 0.01 |
|  |  | Pelex SS-L | 0.01 | 0.01 | 0.01 | 0.01 | 0.01 | — | — | — |
| Concentration of Sustained Release Particles(wt %) [vs Suspension Liquid] |  |  | 25.5 | 25.5 | 25.5 | 25.5 | 25.5 | 25.5 | 25.5 | 25.5 |
| Concentration of Antibiotic Compound(wt %) [vs Suspension Liquid] |  |  | 10.0 | 10.0 | 10.0 | 10.0 | 10.0 | 10.0 | 10.0 | 10.0 |
| Stirring Conditions with Homo Mixer at the time of Water Dispersion | Number of Revolution(rpm) |  | 2000 | 3000 | 3000 | 3000 | 3000 | 3000 | 3000 | 3000 |
| Median Size of Sustained Release Particles(μm) |  |  | 36 | 22 | 19 | 30 | 32 | 24 | 22 | 22 |

[1]containing Isomer IV(Melting Point102° C.)
[2]Hydrophilic

TABLE 4

|  |  |  |  |  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|---|---|
|  |  |  | Molecular-Weight | Melting Point(° C.) |  |  |  |  |  |  |
| Hydrophobic Solution | Antibiotic Compound | IPBC | 281 | 60 | — | — | — | 40 | 40 | 40 |
|  |  | OIT | 213 | <20 | — | — | — | — | — | — |
|  |  | Cyfluthrin | 434 | 57, 74, 66[1] | — | — | — | — | — | — |
|  |  | Propiconazole | 342 | <20 | — | — | — | — | — | — |
|  |  | Prochloraz | 375 | 45 to 52 | — | — | — | — | — | — |
|  |  | Flusilazole | 315 | 54 | — | — | — | — | — | — |
|  |  | MBACT | 253 | 133 | 10 | 40 | — | — | — | — |
|  |  | Capric Acid[2] | 172 | 29 to 32 | — | — | 40 | — | — | — |
|  | Mixing Ratio of Antibiotic Compound relative to Polymerizable Vinyl monomer |  |  |  | 0.11 | 0.67 | 0.67 | 0.67 | 0.67 | 0.67 |
|  | Solubility Parameter $\delta$ [(J/cm$^3$)$^{1/2}$] | Polar Term $\delta_{p, compound}$ |  |  | 7.18 | 7.18 | 2.20 | 3.23 | 3.23 | 3.23 |
|  |  | Hydrogen Bonding Term $\delta_{h, compound}$ |  |  | 8.77 | 8.77 | 7.24 | 7.83 | 7.83 | 7.83 |
| Polymerizable vinyl monomer | Compatible Monomer | Methyl methacrylate |  |  | 81 | 54 | 42 | — | — | — |
|  |  | n-Butyl methacrylate |  |  | — | — | — | 42 | — | — |
|  |  | Methyl acrylate |  |  | — | — | — | — | — | 42 |
|  |  | Ethyl acrylate |  |  | — | — | — | — | — | — |
|  |  | n-Butyl acrylate |  |  | — | — | — | — | — | — |
|  |  | Methacrylic acid |  |  | — | — | — | — | — | — |
|  |  | Styrene |  |  | — | — | — | — | 42 | — |
|  | Crosslinkable Monomer | Ethylene glycol dimethacrylate |  |  | 9 | 6 | 18 | 18 | 18 | 18 |
|  |  | Trimethylolpropane trimethacrylate |  |  | — | — | — | — | — | — |
| Oil-soluble Initiator |  | Dilauroyl peroxide |  |  | 0.3 | 0.3 | 0.3 | 0.3 | 0.3 | 0.3 |
| Ion-Exchange Water |  |  |  |  | 280 | 280 | 280 | 280 | 280 | 280 |
| Polymer | Solubility Parameter $\delta$ [(J/cm$^3$)$^{1/2}$] | Polar Term $\delta_{p, polymer}$ |  |  | 5.92 | 5.92 | 5.80 | 4.25 | 2.50 | 6.76 |
|  |  | Hydrogen Bonding Term $\delta_{h, polymer}$ |  |  | 9.36 | 9.36 | 9.60 | 8.26 | 3.13 | 10.30 |
| $\Delta\delta_p$ | (=$\delta_{p, polymer}$ − $\delta_{p, compound}$)[(J/cm$^3$)$^{1/2}$] |  |  |  | −1.26 | −1.26 | 3.60 | 1.02 | −0.73 | 3.53 |
| $\Delta\delta_h$ | (=$\delta_{h, polymer}$ − $\delta_{h, compound}$)[(J/cm$^3$)$^{1/2}$] |  |  |  | 0.59 | 0.59 | 2.36 | 0.43 | −4.7 | 2.47 |
| Dispersing Agent |  | PVA-217 |  |  | 2 | 2 | — | 2 | — | 2 |
|  |  | TCP-10U |  |  | — | — | 2 | — | 2 | — |
| Surfactant |  | DBN |  |  | 0.01 | 0.01 | — | 0.01 | — | 0.01 |
|  |  | Pelex SS-L |  |  | — | — | 0.01 | — | 0.01 | — |
| Concentration of Sustained Release Particles(wt %) [vs Suspension Liquid] |  |  |  |  | 25.5 | 25.5 | 25.5 | 25.5 | 25.5 | 25.5 |

TABLE 4-continued

|  | Examples and Comparative Examples | | | | | |
|---|---|---|---|---|---|---|
|  | Comp. Ex. 1 | Comp. Ex. 2 | Comp. Ex. 3 | Comp. Ex. 4 | Comp. Ex. 5 | Comp. Ex. 6 |
| Concentration of Antibiotic Compound(wt %) [vs Suspension Liquid] | 2.5 | 10.0 | 10.0 | 10.0 | 10.0 | 10.0 |
| Stirring Conditions with Homo Mixer at the time of Water Dispersion   Number of Revolution(rpm) | 3000 | 3000 | 2000 | 3000 | 3000 | 3000 |
| Median Size of Sustained Release Particles(μm) | 20 | 26 | —*3 | 28 | 30 | 11 |

*[1]Containing Isomer IV(Melting Point102° C.)
*[2]Hydrophilic
*[3]Suspension could not be prepared due to deposits of capric acid

Example 17

Formulation of Powder Formulation and Re-Formulation of Suspension

The suspension liquid of Example 2 was transferred to a stainless steel-made vat, and dried in air at room temperature, thereby formulating powder formulation excellent in flowability.

Then, to 50 g of the formulated powder formulation, deionized water was added so that its solid content concentration was 25%, and the mixture was stirred with T.K. Disper (manufactured by PRIMIX Corporation) so that the powder formulation was dispersed (suspend) in water again, thereby re-formulating (reproducing) the suspension.

The controlled release particles of the re-formulated suspension of Example 17 had the same median size and the same particle size distribution as those of the controlled release particles of the suspension of Example 2.

Examples 18 to 22

Formulation of Powder Formulation and Re-Formulation of Suspension

In Examples 9 to 13 as well, the powder formulation was formulated, and then the suspension was re-formulated in the same manner as Example 17, and the powder formulation and the suspension were used as the powder formulation and the suspension of Examples 18 to 22, respectively.

The re-formulated suspensions of Examples 18 to 22 had the same median size and the particle size distribution as those of the controlled release particles of the suspension of Examples 9 to 13.

Table 5 shows correspondence of the powder formulations and the suspensions (after re-suspension) of Examples 17 to 22, and the suspensions of Examples 2, 9 to 13.

TABLE 5

| Form | Suspension | Ex. 2 | Ex. 9 | Ex. 10 | Ex. 11 | Ex. 12 | Ex. 13 |
|---|---|---|---|---|---|---|---|
|  | Powder Formulation | Ex. 17 | Ex. 18 | Ex. 19 | Ex. 20 | Ex. 21 | Ex. 22 |
|  | Suspension (after re-suspension) |  |  |  |  |  |  |

Calculation of Solubility Parameter (δ)

1. The Polar Term $\delta_{p,polymer}$ and the Hydrogen Bonding Term $\delta_{h,polymer}$ of the Solubility Parameter (δ) of the Polymer were Calculated as Described Above.

Table 2 to Table 4 show the results of calculation along with the polar term $\delta_{p,compound}$ and the hydrogen bonding term $\delta_{h,compound}$ of the solubility parameter (δ) of the antibiotic compound (ref: Table 1).

2. $\Delta\delta_p(=\delta_{p,polymer}-\delta_{p,compound})$ and $\Delta\delta_h(=\delta_{h,polymer}-\delta_{h,compound})$ are Calculated.

The results are shown in Table 2 to Table 4.

Evaluation

1. SEM (Scanning Electron Microscope) Observation

The suspension liquids (suspension) of Examples 1 to 16 and Comparative Examples 2, 4 to 6 were dropped on a stage, and thereafter, water was vaporized away, thereby producing controlled release particles (particles in Comparative Examples 2 and 4 to 6). The controlled release particles (particles) were observed with a scanning electron microscope (Hitachi TM-100 manufactured by Hitachi High-Technologies Corporation).

FIGS. 1 to 10 show image-processed SEM photograph of Examples 1, 5, 8, 14 to 16 and Comparative Examples 2, 4 to 6, respectively.

As shown in the examples of FIGS. 1 to 6, in any of Examples 1 to 16, no antibiotic compound deposited outside the controlled release particles.

Figure 7:
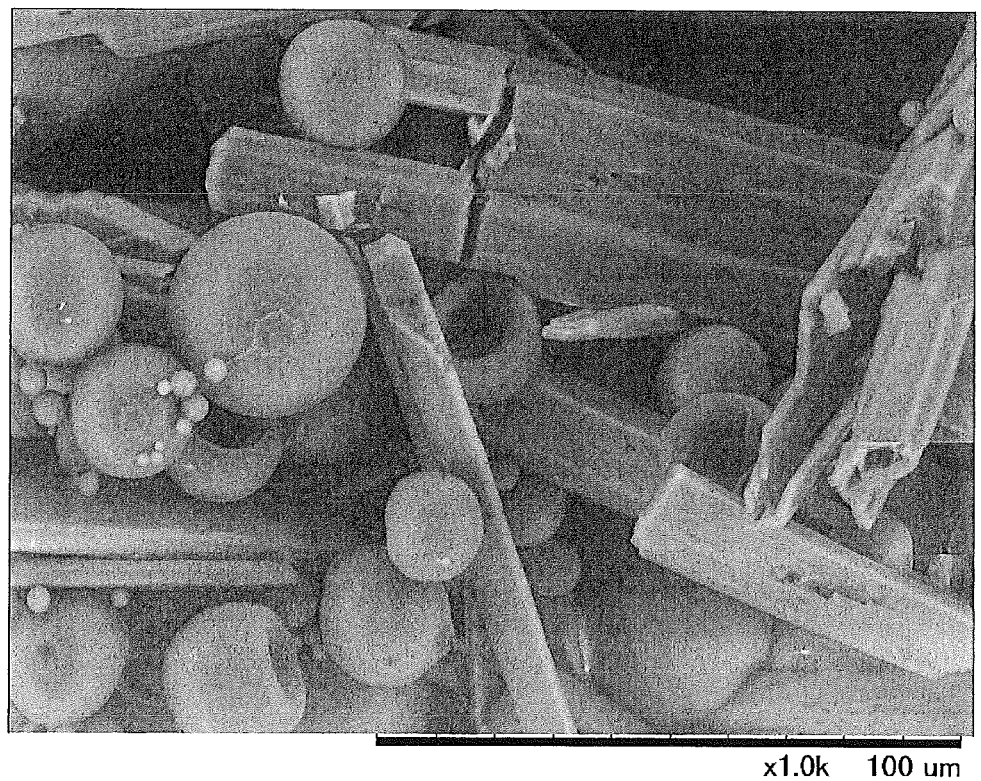
FIG. 7 shows an image-processed SEM photograph of particles of Comparative Example 2.

On the other hand, as can be seen in FIG. 7, in Comparative Example 2, it was found that the antibiotic compound deposited outside the controlled release particles in the form of needle crystal, and furthermore, the particles were formed into a generally bowl shape. That is, it was confirmed that holes that were caused by phase separation and discharge of the antibiotic compound to the outside were formed.

Figure 8:
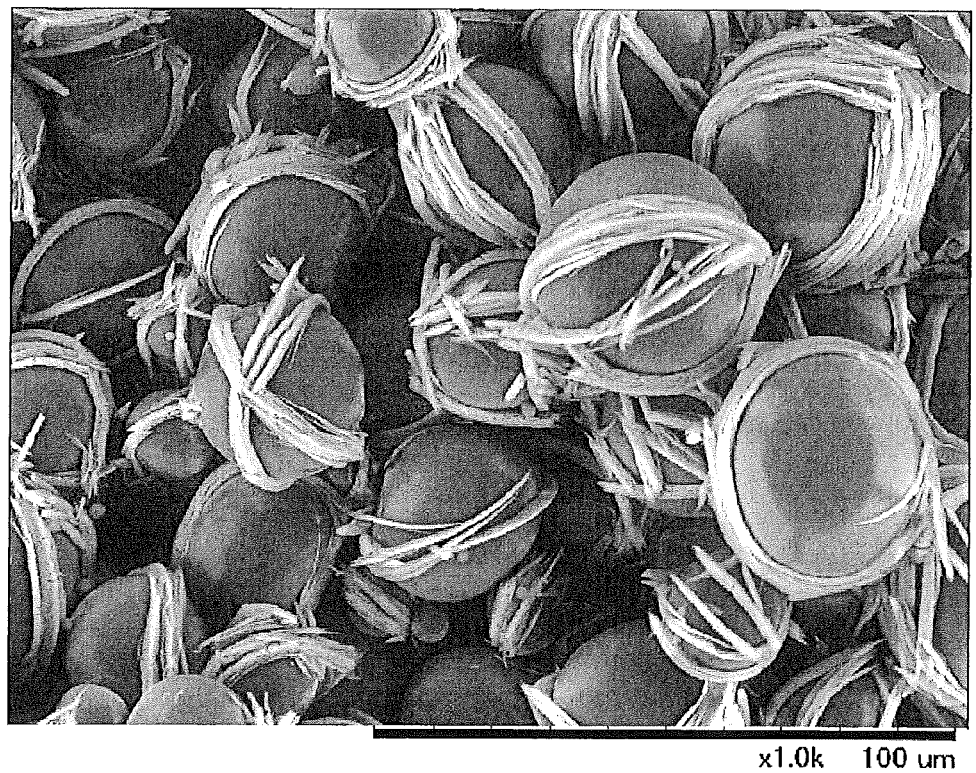
FIG. 8 shows an image-processed SEM photograph of particles of Comparative Example 4.

Furthermore, as can be seen from FIG. 8, in Comparative Example 4, it was found that the antibiotic compound deposited in the form of needle crystal in a manner such that the antibiotic compound was wound around the periphery of the particles.

Figure 9:
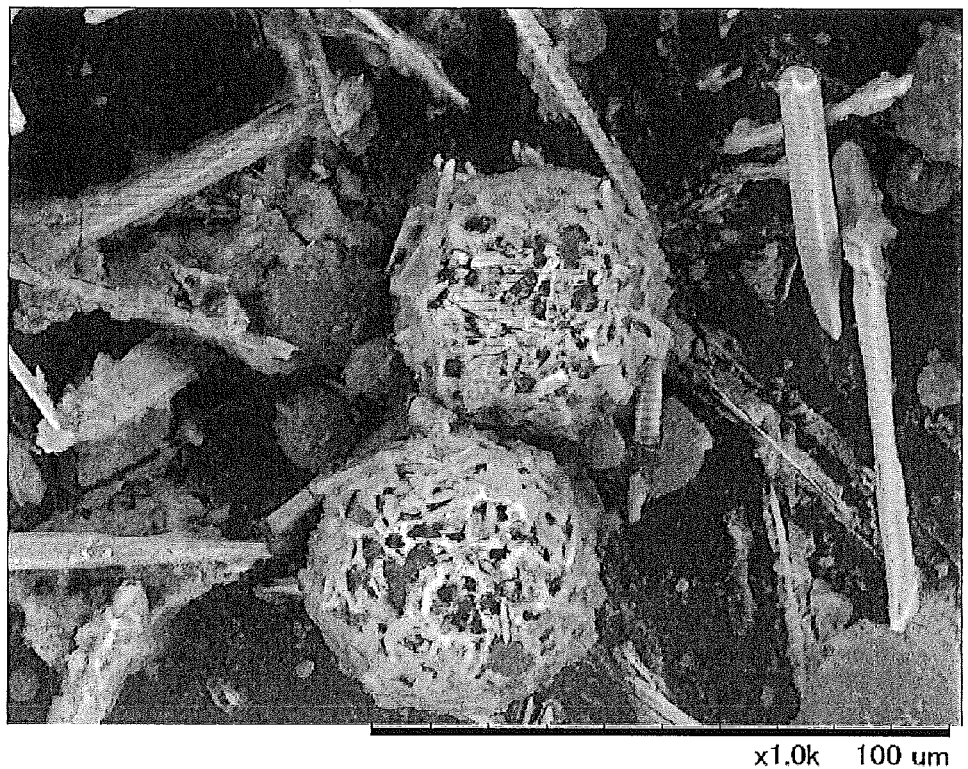
FIG. 9 shows an image-processed SEM photograph of particles of Comparative Example 5.

Furthermore, as can be seen from FIG. 9, it was found that in Comparative Example 5, a portion of the antibiotic compound deposited in the form of needle crystal and the remaining portion of the antibiotic compound covered the surface of the particles.

Figure 10:
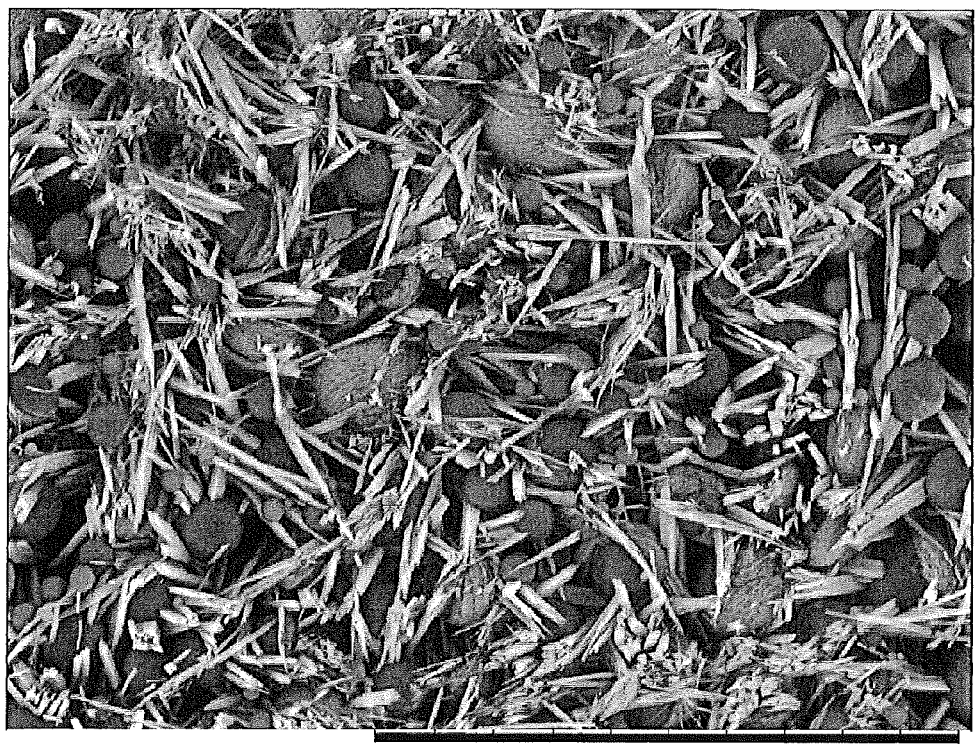
FIG. 10 shows an image-processed SEM photograph of particles of Comparative Example 6.

Furthermore, as can be seen from FIG. 10, it was found that in Comparative Example 6, the antibiotic compound deposited outside the controlled release particles in the form of needle crystal.

In Example 6, due to the effects of OIT as the plasticizer, a transparent film was formed after evaporation of water, and therefore no SEM observation could be conducted. Thus, the fact shows that the controlled release particles of Example 6 were in a miscibly blended state.

2. TEM (Transmission Electron Microscope) Observation

The suspension liquids (suspensions) of Examples 1 to 16 were freeze-dried, then dispersed in a bisphenol liquid epoxy resin containing amine, and thereafter cured. Then, the cured product was cut with an ultramicrotome to expose its cross section; the cross section was dyed with osmium tetroxide, and as necessary, also with ruthenium tetroxide; the cross section was cut out with an ultramicrotome into extremely thin slices, thereby preparing samples. The prepared samples were observed with a transmission electron microscope (model number "H-7100", manufactured by Hitachi, Ltd.).

FIGS. 11 to 16 show image-processed TEM photograph of Examples 1 and 9 to 13, respectively.

As shown in the examples of FIGS. 11 to 16, it was found that in any of Examples 1 and 9 to 13, the antibiotic compound was contained in the controlled release particles.

Figure 11:
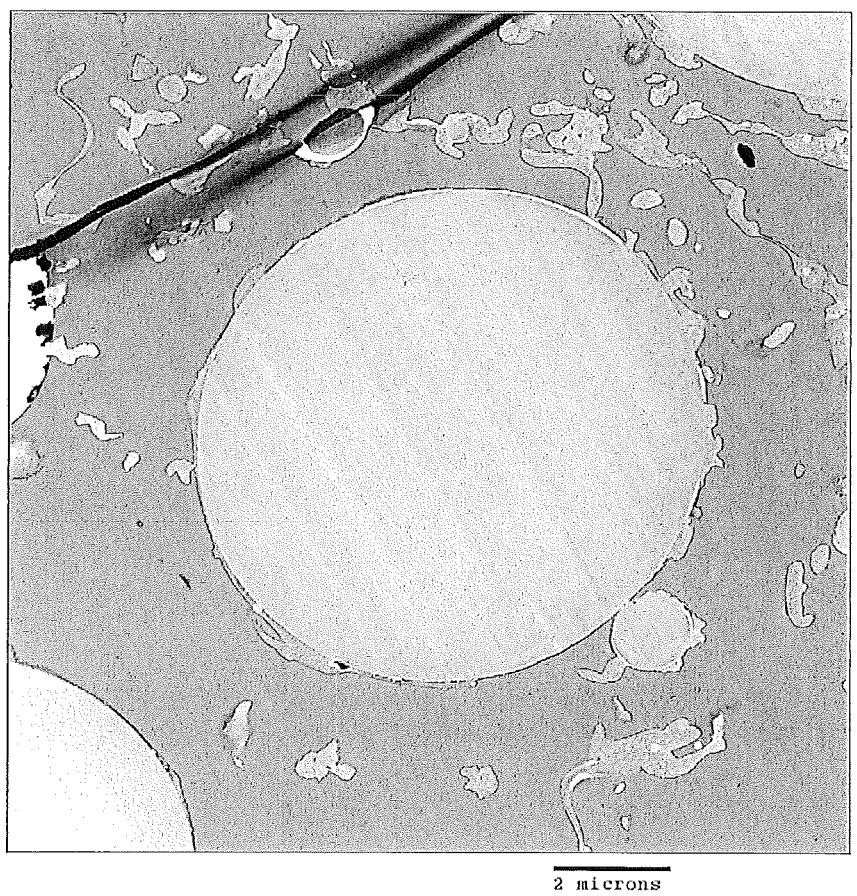
FIG. 11 shows an image-processed TEM photograph of controlled release particles of Example 1.
Figure 12:
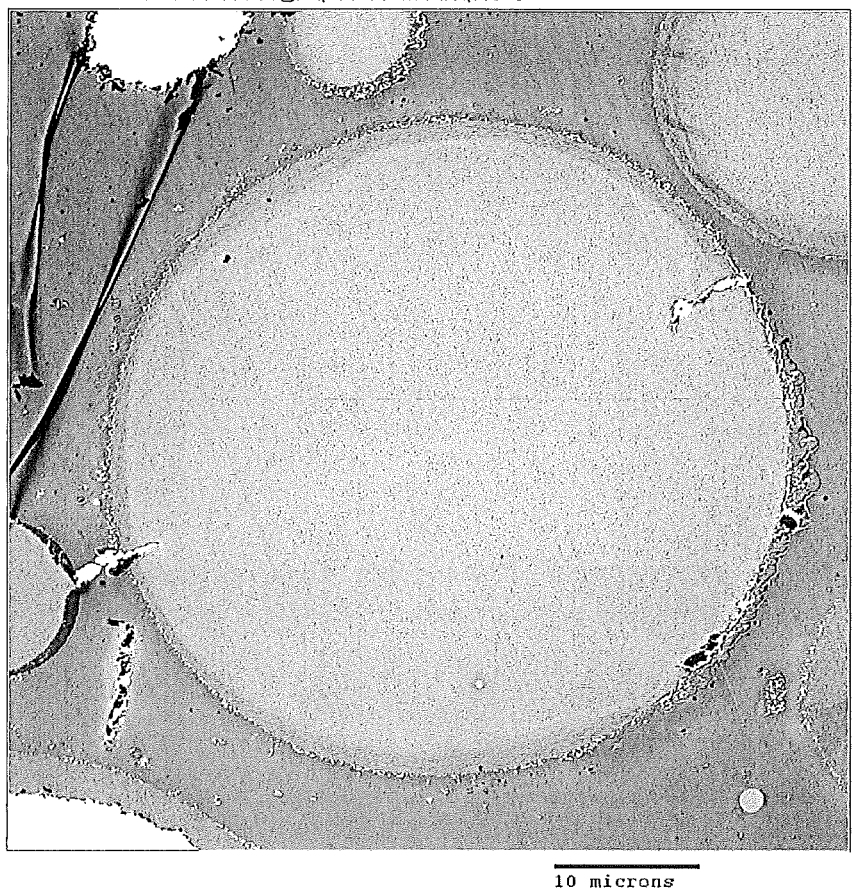
FIG. 12 shows an image-processed TEM photograph of controlled release particles of Example 9.
Figure 14:
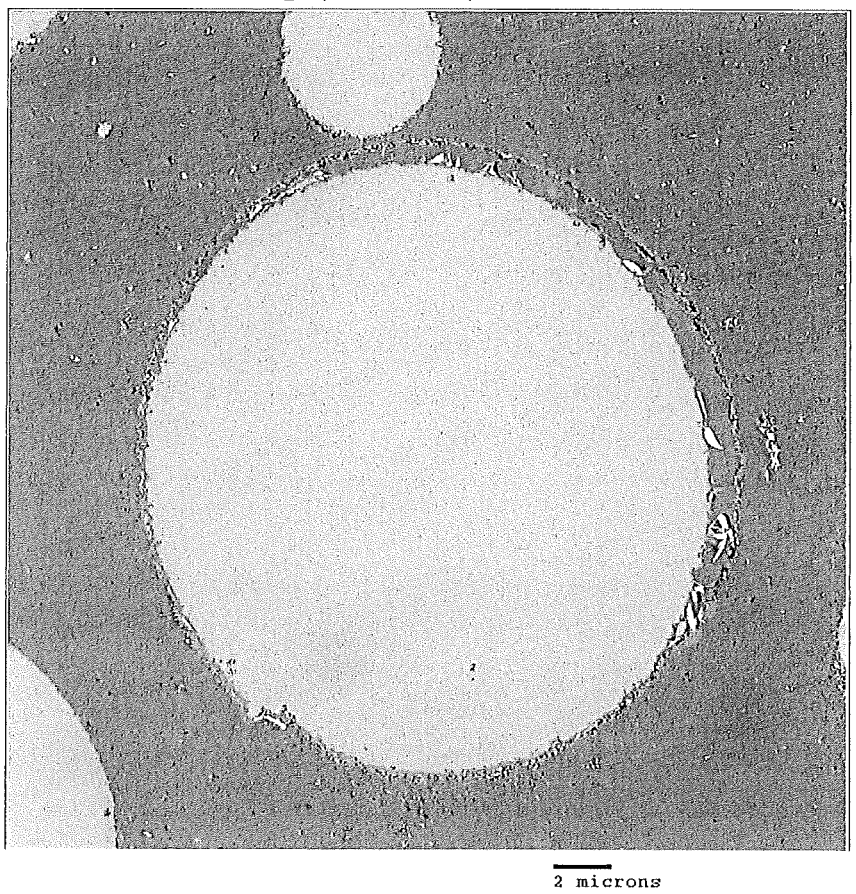
FIG. 14 shows an image-processed TEM photograph of controlled release particles of Example 11.

In particular, as is clear from FIG. 11, FIG. 12, and FIG. 14, it was found that the antibiotic compound was miscibly blended homogeneously and contained in the controlled release particles in Examples 1, 9, and 11, because the cross sections of the controlled release particles were uniform.

Figure 13:
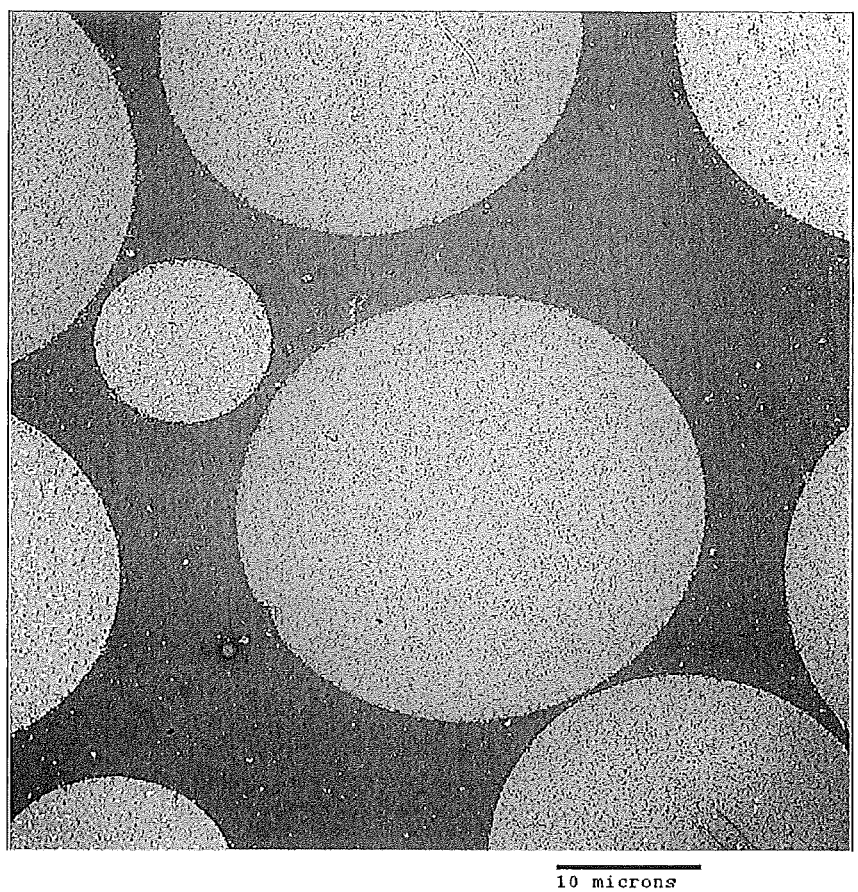
FIG. 13 shows an image-processed TEM photograph of controlled release particles of Example 10.

Furthermore, as can be seen from FIG. 13, in Example 10, it was found that the antibiotic compound of the present invention, that is, a mixture of isomer I (inciting point: 57° C.), isomer II (melting point: 74° C.), and isomer III (inciting point: 66° C.) of cyfluthrin was homogeneously blended and contained in the polymer, while isomer IV (inciting point: 102° C.), which is contained as an impurity in an amount of about 20 wt % deposited inside of the polymer, thereby allowing the controlled release particles to be formed in a microphase separation state.

Figure 15:
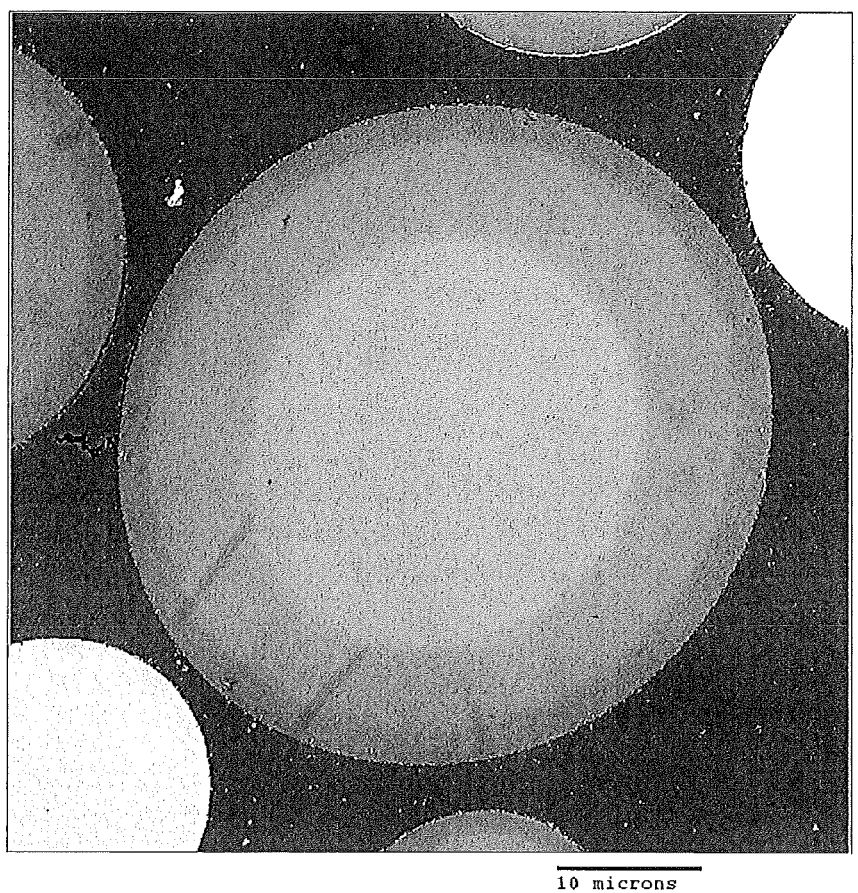
FIG. 15 shows an image-processed TEM photograph of controlled release particles of Example 12.
Figure 16:
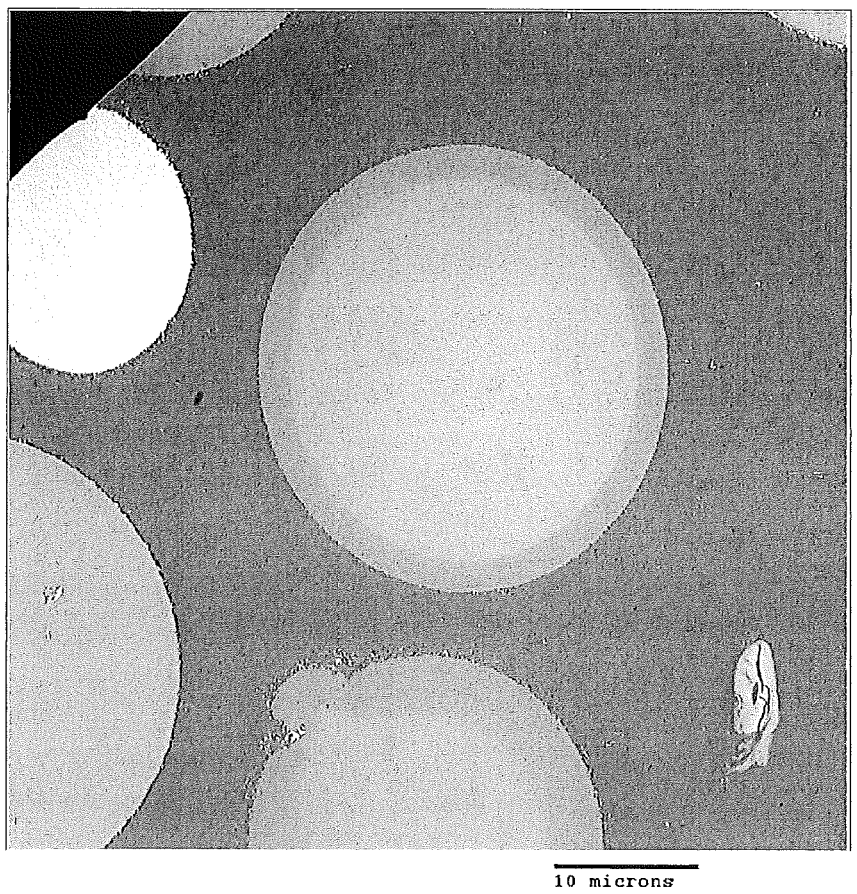
FIG. 16 shows an image-processed TEM photograph of controlled release particles of Example 13.

Furthermore, as can be seen from FIGS. 15 and 16, in Examples 12 and 13, the concentration gradient of the antibiotic compound in the polymer was confirmed as light and shade. That is, on the surface of the controlled release particles, a dark shade represents a high concentration of the antibiotic compound, and at the center of the controlled release particles, a light shade represent a low antibiotic compound concentration. It was also found that while the antibiotic compound was miscibly blended into the polymer, the concentration of the antibiotic compound increased from the center toward the surface of the controlled release particles.

3. Controlled Release Properties Test (1) Controlled Release Properties Test of IPBC-containing Controlled Release Particles (Examples 1 to 3 and 14 to 16)

Controlled release properties test was conducted for the IPBC-containing controlled release particles of Examples 1 to 3 and 14 to 16 in the following manner.

That is, first, suspension liquids (IPBC concentration 10 wt %) of the controlled release particles of Examples 1 to 3 and 14 to 16; and a blank IPBC suspension liquid (IPBC concentration 10 wt %) in which IPBC was suspended were prepared.

Then, two sheets of circular filter paper (Toyo Roshi Kaisha, Ltd. No. 5C, corresponds to type 5C of JIS P 3801) were piled and folded to be pleated.

Then, 0.5 mL of the prepared suspension liquids were slowly poured individually onto the filter papers, and thereafter dried in air.

To the filter paper, water in an amount of 1000 mL was passed through using a metered-dose tube pump at a flow rate of 20 mL/hr, and controlled-release rate of the IPBC was calculated using HPLC based on the IPBC amount of the obtained filtrate and the IPBC amount remained in the filter paper. The controlled-release rate in each amount of water passed through was calculated as cumulative value (that is, total controlled-release rate).

Figure 17:
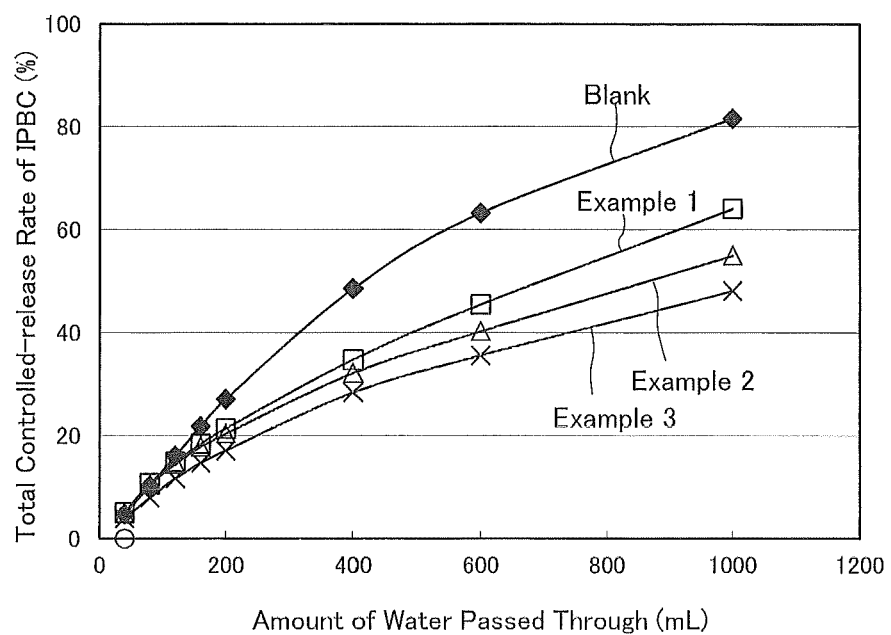
FIG. 17 shows a graph of controlled release properties test of Examples 1 to 3.
Figure 18:
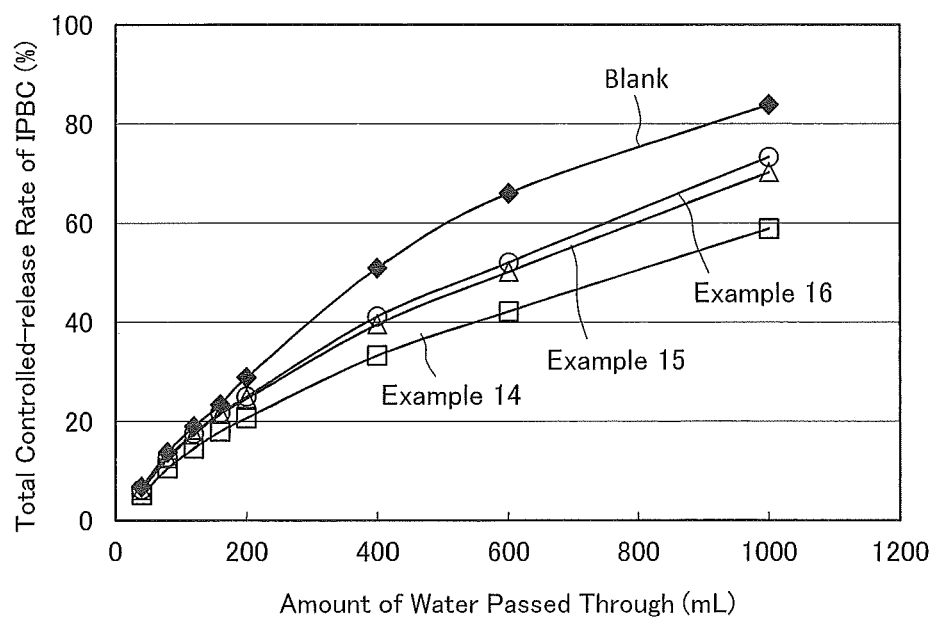
FIG. 18 shows a graph of controlled release properties test of Examples 14 to 16.

FIG. 17 shows the results of Examples 1 to 3, and FIG. 18 shows the results of Examples 14 to 16.

(2) Controlled Release Properties Test for Propiconazole-Containing Controlled Release Particles (Example 11)

Controlled release properties test for propiconazole-containing controlled release particles of Example 11 was conducted in the same manner as the above-described "(1) controlled release properties test for IPBC-containing controlled release particles".

Figure 19:
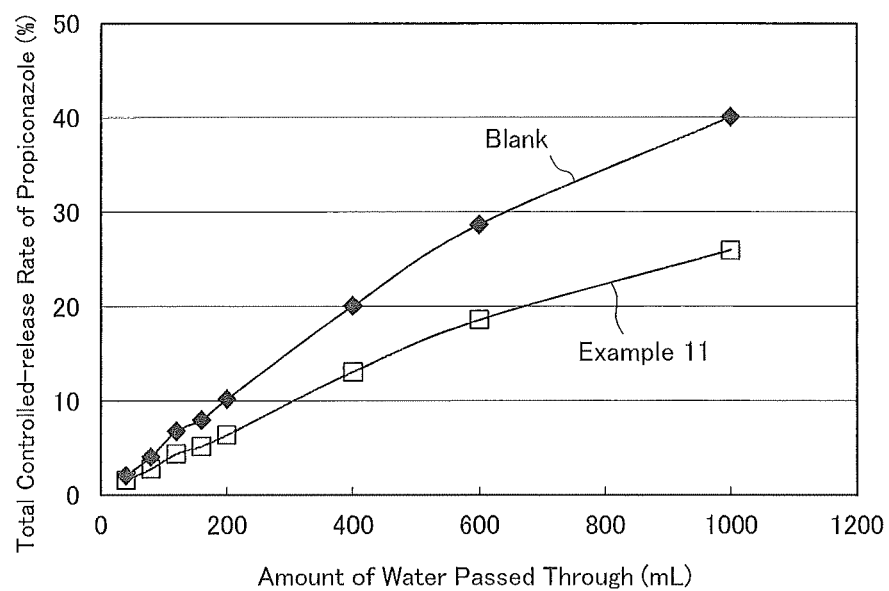
FIG. 19 shows a graph of controlled release properties test of Example 11.

The results are shown in FIG. 19.

(3) Controlled Release Properties Test for Prochloraz-Containing Controlled Release Particles (Example 12)

Controlled release properties test for prochloraz-containing controlled release particles of Example 12 was conducted in the same manner as the above-described "(1) controlled release properties test for IPBC-containing controlled release particles".

Figure 20:
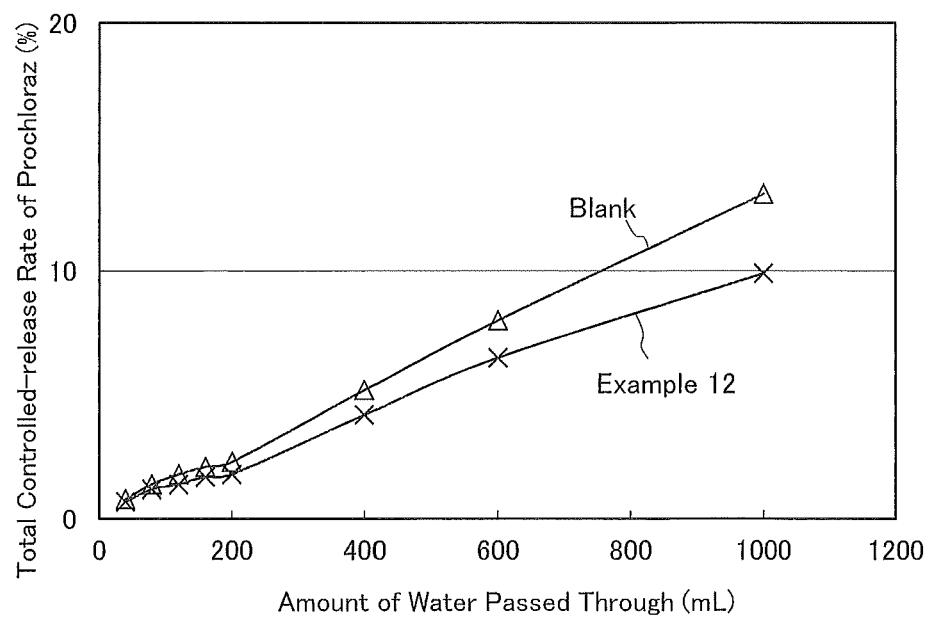
FIG. 20 shows a graph of controlled release properties test of Example 12.

The results are shown in FIG. 20.

(4) Controlled Release Properties Test for Flusilazole-Containing Controlled Release Particles (Example 13)

Controlled release properties test for flusilazole-containing controlled release particles of Example 13 was conducted in the same manner as the above-described "(1) controlled release properties test of IPBC-containing controlled release particles".

Figure 21:
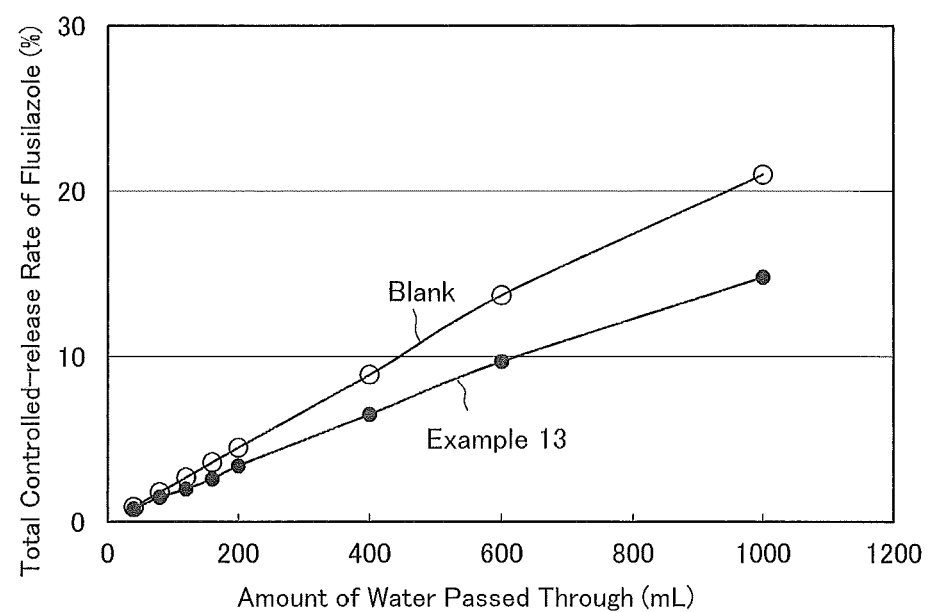
FIG. 21 shows a graph of controlled release properties test of Example 13.

The results are shown in FIG. 21.

(5) Controlled Release Properties Test for OIT-Containing Controlled Release Particles (Examples 4 to 7, and 9)

Controlled release properties test for OIT-containing controlled release particles of Examples 4 to 7, and 9 was conducted in the following manner.

First, to a commercially available white acrylic silicone emulsion paint, suspension liquids (suspensions) of controlled release particles obtained in Examples 4 to 7 and 9, and a blank OIT were added so that the OIT concentration was 0.2 wt % in each liquid, and thereafter, the paint to which the suspension liquid of the controlled release particles was added was diluted with ion-exchange water to 1.5 times.

Then, a filter paper (Toyo Roshi Kaisha, Ltd. No. 2, corresponding to type 2 of JIS P 3801) was cut out to a size of 3.5 cm×3.5 cm and weighed, and impregnated with the above-described paint.

Thereafter, the filter paper was put in a glass bottle, 15 mL of ion-exchange water was added thereto, and they were shaken for 18 hours. Then, the ion-exchange water was collected, 15 mL of another ion-exchange water was added thereto, they were shaken for 18 hours. Thereafter, the above-described ion-exchange water exchange operation was repeated twice.

Controlled-release rate of OIT was calculated using HPLC based on the OIT amount in each of the collected ion-exchange water as described above. The controlled-release rate in the each collected ion-exchange water was calculated as cumulative value (that is, total controlled-release rate).

Figure 22:
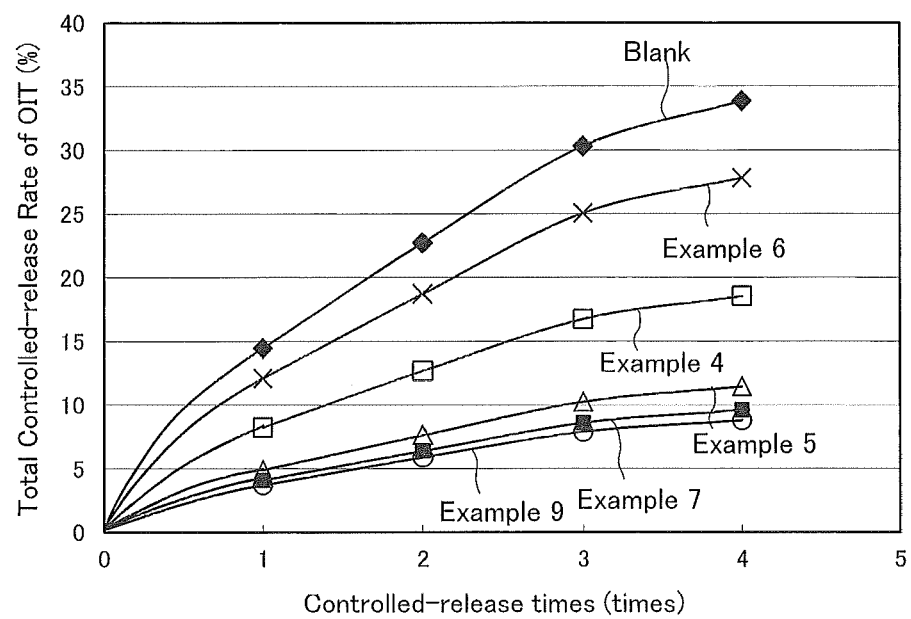
FIG. 22 shows a graph of controlled release properties test of Examples 4 to 7, and 9.

The results are shown in FIG. 22.

(6) Controlled Release Properties Test for Cyfluthrin-Containing Controlled Release Particles (Examples 8 and 10)

Controlled release properties test was conducted for the cyfluthrin-containing controlled release particles of Examples 8 and 10 in the following manner.

That is, a suspension liquid (suspension) of controlled release particles (cyfluthrin concentration 10%) of Examples 8 and 10, a blank acetonitrile (10%) solution in which cyfluthrin was dissolved were prepared.

Then, two sheets of circular filter paper (Toyo Roshi Kaisha, Ltd. No. 5C, corresponds to type 5C JIS P 3801) were piled and pleated.

Then, to the filter paper, 0.5 mL of the prepared suspensions of Examples 8 and 10, and 0.5 mL of the solution of cyfluthrin in acetonitrile were poured slowly, and thereafter dried in air.

Thereafter, the filter paper was put into a glass bottle, and 180 mL of ion-exchange water/methanol (=50/50 (volume ratio)) mixture liquid was added thereto, and allowed to stand and to be impregnated at room temperature for 20 hours. Then, the ion-exchange water/methanol mixture liquid was collected, 180 mL of another ion-exchange water/methanol mixture liquid was added thereto, and allowed to stand and to be impregnated for 20 hours. Thereafter, the above-described ion-exchange water/methanol mixture liquid exchange operation was repeated twice.

The controlled-release amount of the cyfluthrin was calculated using TOF-MS based on the each of the ion-exchange water/methanol mixture liquids collected as described above. The controlled-release amount in the each mixture was calculated as cumulative value (that is, total controlled-release amount).

Figure 23:
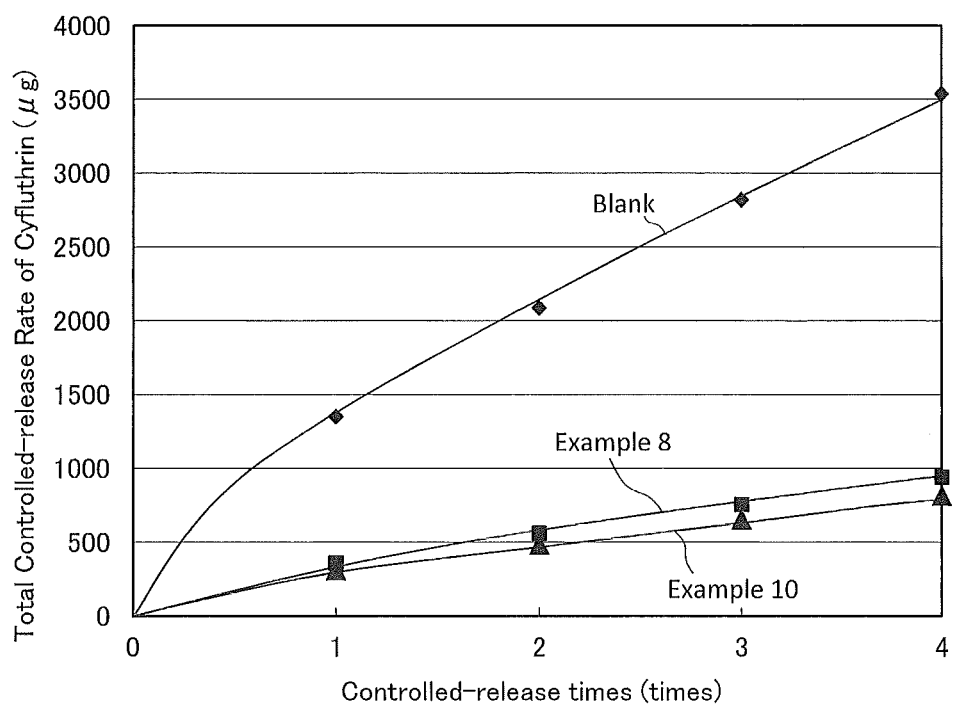
FIG. 23 shows a graph of controlled release properties test of Examples 8 and 10.
Figure 2:
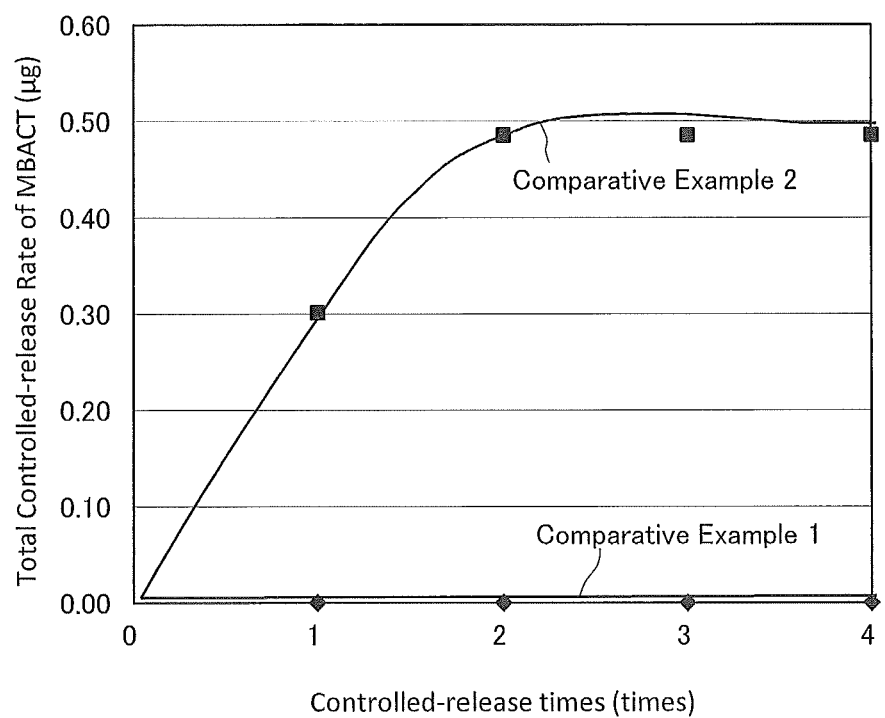
FIG. 2 shows an image-processed SEM photograph of controlled release particles of Example 5.

The results are shown in FIG. 23.

(7) Controlled Release Properties Test for MBACT-Containing Controlled Release Particles (Comparative Example 1) and MBACT-Coexisting Controlled Release Particles (Comparative Example 2)

Controlled release properties test for MBACT was conducted in the same manner as the controlled release properties test for above-described (5) OIT-containing controlled release particles, except that MBACT-containing controlled release particles (Comparative Example 1) and MBACT-coexisting controlled release particles (Comparative Example 2) were used instead of OIT-containing controlled release particles.

The results are shown in FIG. 24.

While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

INDUSTRIAL APPLICABILITY

Controlled release particles of the present invention can be applied to various industrial products, for example, can be blended in indoor/outdoor paint, rubber, fiber, resin, plastic, adhesive, joint mixture, sealing agent, building material, caulking agent, soil treating agent, lumber, white water in paper-making processes, pigment, treatment liquid for printing plates, cooling water, ink, cutting oil, cosmetic products, nonwoven fabric, spinning oil, leather.

The invention claimed is:

1. Controlled release particles obtained by
dissolving a hydrophobic antibiotic compound in a hydrophobic polymerizable vinyl monomer without the presence of a solvent, thereby preparing a hydrophobic solution,
the hydrophobic antibiotic compound having a melting point of 100° C. or less, a polar term $\delta_{p,compound}$ of 2 to 8 $[(J/cm^3)^{1/2}]$ of a solubility parameter ($\delta$), and a hydrogen bonding term $\delta_{h,compound}$ of 5.5 to 9.5 $[(J/cm^3)^{1/2}]$ of the solubility parameter ($\delta$), the solubility parameter ($\delta$) being defined by Hansen and calculated by van Krevelen and Hoftyzer method;
dispersing the hydrophobic solution in water; and
polymerizing the polymerizable vinyl monomer in the presence of an oil-soluble initiator by radical polymerization, thereby producing a polymer having a polar term $\delta_{p,polymer}$ of 5 to 7 $[(J/cm^3)^{1/2}]$ of the solubility parameter ($\delta$) and a hydrogen bonding term $\delta_{h,polymer}$ of 8 to 10 $[(J/cm^3)^{1/2}]$ of the solubility parameter ($\delta$),
the controlled release particles having a homogeneous phase including the polymer and the antibiotic compound.

2. The controlled release particles according to claim 1, wherein the value of $\Delta\delta_p$ obtained by deducting the polar term $\delta_{p,compound}$ of the antibiotic compound from the polar term $\delta_{p,polymer}$ of the polymer is −1.1 to 2.7 $[(J/cm^3)^{1/2}]$, and
the value of $\Delta\delta_h$ obtained by deducting the hydrogen bonding term $\delta_{h,compound}$ of the antibiotic compound from the hydrogen bonding term $\delta_{h,polymer}$ of the polymer is 0 to 4.2 $[(J/cm^3)^{1/2}]$.

3. The controlled release particles according to claim 1, wherein the mixing ratio of the antibiotic compound relative to the polymerizable vinyl monomer is 0.11 to 1.5 on a weight basis.

* * * * *